US011333646B2

(12) United States Patent
Potyrailo

(10) Patent No.: US 11,333,646 B2
(45) Date of Patent: May 17, 2022

(54) GAS SENSOR SYSTEM AND METHOD

(71) Applicant: General Electric Company, Schenectady, NY (US)

(72) Inventor: Radislav Alexandrovich Potyrailo, Niskayuna, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 135 days.

(21) Appl. No.: 16/432,050

(22) Filed: Jun. 5, 2019

(65) Prior Publication Data

US 2020/0386728 A1    Dec. 10, 2020

(51) Int. Cl.
| | | |
|---|---|---|
| *G01N 31/22* | (2006.01) | |
| *A61B 5/00* | (2006.01) | |
| *G01N 33/50* | (2006.01) | |
| *G01N 33/00* | (2006.01) | |
| *G01N 27/22* | (2006.01) | |

(Continued)

(52) U.S. Cl.
CPC ......... *G01N 31/223* (2013.01); *A61B 5/6801* (2013.01); *G01N 27/221* (2013.01); *G01N 33/0031* (2013.01); *G01N 33/50* (2013.01); *G01N 27/02* (2013.01); *G01N 27/026* (2013.01); *G01N 27/04* (2013.01)

(58) Field of Classification Search
CPC .. G01N 31/223; G01N 27/221; G01N 27/026; G01N 27/02; G01N 27/04; G01N 33/50; G01N 33/0031; A61B 5/6801
See application file for complete search history.

(56) References Cited

U.S. PATENT DOCUMENTS

| | | |
|---|---|---|
| 5,403,746 A | 4/1995 | Bentsen et al. |
| 7,053,425 B2 | 5/2006 | Sandvik et al. |
| 7,763,208 B2 | 7/2010 | Steichen et al. |
| | (Continued) | |

FOREIGN PATENT DOCUMENTS

| | | | | |
|---|---|---|---|---|
| DE | 10308799 A1 | * | 9/2004 | ........... G01N 27/125 |
| EP | 1026501 A2 | * | 8/2000 | ......... G01N 27/4067 |

OTHER PUBLICATIONS

Schierbaum et al., "Multicomponent gas analysis: An analytical chemistry approach applied to modified SnO2", Sensors and Actuators B: Chemical, vol. 2, Issue: 1, pp. 71-78, Mar. 1990.

(Continued)

*Primary Examiner* — David L Singer
*Assistant Examiner* — Fatemeh Esfandiari Nia
(74) *Attorney, Agent, or Firm* — Fletcher Yoder, P.C.

(57) ABSTRACT

A gas sensor system includes a gas sensing element that includes a gas sensing material and electrodes configured to apply electrical stimuli to the gas sensing material and one or more processors configured to control the gas sensing element. The one or more processors are configured to direct the electrodes to apply the electrical stimuli at two or more different electrical excitation frequencies to the gas sensing material. A first electrical excitation frequency of the two or more different electrical excitation frequencies is configured to provide a quantitative gas response of the gas sensing material, the quantitative gas response including a response drift. A second electrical excitation frequency of the two or more different electrical excitation frequencies is configured to provide a baseline response of the gas sensing material based at least in part on the response drift.

26 Claims, 14 Drawing Sheets

(51) Int. Cl.
G01N 27/02 (2006.01)
G01N 27/04 (2006.01)

(56) References Cited

U.S. PATENT DOCUMENTS

| | | | |
|---|---|---|---|
| 7,911,345 B2 | 3/2011 | Potyrailo et al. | |
| 8,357,958 B2 | 1/2013 | Cummins | |
| 8,884,382 B2 | 11/2014 | Stetter et al. | |
| 9,030,329 B2 | 5/2015 | Rutherford et al. | |
| 9,304,101 B1 | 4/2016 | Farber | |
| 2006/0155486 A1* | 7/2006 | Walsh | G01N 33/0034 702/32 |
| 2007/0202012 A1* | 8/2007 | Steichen | G01N 33/0031 422/98 |
| 2008/0067080 A1* | 3/2008 | Martin | G01N 27/4074 205/785.5 |
| 2010/0188110 A1* | 7/2010 | Sun | G01N 33/0031 324/694 |
| 2014/0028327 A1* | 1/2014 | Potyrailo | G01N 33/0073 324/601 |
| 2015/0115983 A1* | 4/2015 | Potyrailo | G01N 33/2888 324/693 |
| 2018/0372662 A1 | 12/2018 | Boudaden et al. | |
| 2020/0173945 A1* | 6/2020 | Burdack-Freitag | G01N 33/0006 |
| 2020/0209193 A1* | 7/2020 | Swett | E21B 47/07 |

OTHER PUBLICATIONS

Gutierrez et al., "Use of complex impedance spectroscopy in chemical sensor characterization", Sensors and Actuators B: Chemical, vol. 4, Issues: 3-4, pp. 359-363, Jun. 1991.

Endres et al., "Impedance spectroscopy on dielectric gas sensors", Impedance spectroscopy on dielectric gas sensors, Sensors and Actuators B: Chemical, vol. 22, Issue: 1, pp. 7-11, Oct. 1994.

Kurzweil et al., "Impedance of zeolite-based gas sensors", Sensors and Actuators B: Chemical, vol. 25, Issues: 1-3, pp. 653-656, Apr. 1995.

Weimar et al., "A.c.Measurements on Tin Oxide Sensors to Improve Selectivities and Sensitivities", Sensors and Actuators B: Chemical, vol. 26, Issues: 1-3, pp. 13-18, 1995.

Chiorino et al., "Characterization of SnO2-based gas sensors. A spectroscopic and electrical study of thick films from commercial and laboratory-prepared samples", Sensors and Actuators B: Chemical, vol. 44, Issues: 1-3, pp. 474-482, Oct. 1997.

Varghese et al., "Studies of ambient dependent electrical behavior of nanocrystalline SnO2 thin films using impedance spectroscopy", Journal of Applied Physics, vol. 87, Issue: 10, pp. 7457-7465, 2000.

Kiss et al., "Study of oxide semiconductor sensor materials by selected methods", Thin Solid Films, vol. 391, Issue: 2, pp. 216-223, Jul. 16, 2001.

Kaur et al., "Detection of reducing gases by SnO2 thin films: an impedance spectroscopy study", Sensors and Actuators B: Chemical, vol. 107, Issue: 1, pp. 360-365, May 27, 2005.

Chakraborty et al., "Complex plane impedance plot as a figure of merit for tin dioxide-based methane sensors", Sensors and Actuators B: Chemical, vol. 119, Issue: 2, pp. 431-434, Dec. 7, 2006.

Rheaume et al., "A review of recent progress in sensing of gas concentration by impedance change", International Journal of Ionics The Science and Technology of Ionic Motion, vol. 17, Issue: 2, pp. 99-108, Mar. 2011.

Huan et al., "Analysis of the aging characteristics of SnO2 gas sensors", Sensors and Actuators B: Chemical, vol. 156, Issue: 2, pp. 912-917, Aug. 2011.

Betty et al., "Discerning specific gas sensing at room temperature by ultra thin SnO2 films using impedance approach", Sensors and Actuators B: Chemical, vol. 173, pp. 781-788, Oct. 2012.

Boeker et al., "On 'Electronic Nose' methodology", Sensors and Actuators B: Chemical, vol. 204, pp. 2-17, Dec. 1, 2014.

Lee et al., "Electrodes for Semiconductor Gas Sensors", Sensors (Basel), vol. 17, Issue: 4, Apr. 2017.

\* cited by examiner

GAS SENSOR SYSTEM AND METHOD

GOVERNMENT LICENSE RIGHTS

This invention was made with government support under contract 75D30118C02617 awarded by the National Institute For Occupational Safety And Health. The government has certain rights in the invention.

FIELD

One or more embodiments are disclosed that relate to systems and methods for sensing gases.

BACKGROUND

Drift of gas sensors represents a limitation toward expanding industrial and/or consumer applications of sensor systems where long-term stability of installed sensors is critical. To address this challenge of response drift, different approaches have been made, such as sensor systems periodically being recalibrated by removing them from a measurement system. Another approach includes calibrating sensors without removing the sensor from the system but by bringing carrier gas to the sensor. Another approach includes a sensor being re-charged and calibrated daily. However, these approaches have limitations including requiring calibrations with an analyte gas that occur more frequently than a maintenance cycle of the sensor system, and requiring a calibration gas to be presented to the sensor.

Metal oxide semiconductor (MOS) sensors are common because of the ability to detect numerous gases by the selection of the base semiconductor material and its doping. However, the response drift of MOS sensors is a limitation in emerging applications. Impedance measurements of metal oxide semiconductor sensors are well known to allow more selective sensor responses but do not describe solutions to solve the drift problems without inspecting the sensor. One correction method includes turning the sensor off, inspecting its intrinsic properties, and turning the sensor back on.

BRIEF DESCRIPTION

In one embodiment, a gas sensor system includes a gas sensing element that includes a gas sensing material and electrodes configured to apply electrical stimuli to the gas sensing material and one or more processors configured to control the gas sensing element. The one or more processors are configured to direct the electrodes to apply the electrical stimuli at two or more different electrical excitation frequencies to the gas sensing material. A first electrical excitation frequency of the two or more different electrical excitation frequencies is configured to provide a quantitative gas response of the gas sensing material, the quantitative gas response including a response drift. A second electrical excitation frequency of the two or more different electrical excitation frequencies is configured to provide a baseline response of the gas sensing material based at least in part on the response drift.

In one embodiment, a method includes applying a first electrical stimuli to a gas sensing material of a gas sensing element via electrodes at a first electrical excitation frequency and receiving a quantitative gas response of the gas sensing material responsive to applying the first electrical stimuli at the first electrical excitation frequency to the gas sensing material. The quantitative gas response includes a response drift. The method also includes applying a second electrical stimuli to the gas sensing material of the gas sensing element via the electrodes at a second electrical excitation frequency. The second electrical excitation frequency is configured to provide a baseline response of the gas sensing material to the response drift.

In one embodiment, a gas sensor system includes a gas sensing element that includes a gas sensing material and electrodes configured to apply electrical stimuli to the gas sensing material and one or more processors configured to control the gas sensing element. The one or more processors are configured to direct the electrodes to apply the electrical stimuli at two or more different electrical excitation frequencies to the gas sensing material when the gas sensor system is in an operating state. A first electrical excitation frequency of the two or more different electrical excitation frequencies is configured to provide a quantitative gas response of the gas sensing material. A second electrical excitation frequency of the two or more different electrical excitation frequencies is configured to improve a limit of detection of a gas of interest of the quantitative gas response of the gas sensing material relative to the first electrical excitation frequency.

In one embodiment, a gas sensor system includes a gas sensing element that includes a gas sensing material and electrodes configured to apply electrical stimuli to the gas sensing material and one or more processors configured to control the gas sensing element, wherein the one or more processors are configured to direct the electrodes to apply the electrical stimuli at two or more different electrical excitation conditions to the gas sensing material. A first electrical excitation condition of the two or more different electrical excitation conditions is configured to provide a quantitative gas response of the gas sensing material, the quantitative gas response including a response drift. A second electrical excitation condition of the two or more different electrical excitation conditions is configured to provide a baseline response of the gas sensing material based at least in part on the response drift.

DETAILED DESCRIPTION

One or more embodiments of the inventive subject matter described herein provide gas sensing systems and methods that provide correction of response drift without powering off the sensor and without requiring a calibration gas to calibrate the sensor. The systems and methods apply electrical stimuli at two different electrical excitation frequencies to a gas sensing material of the system. A first electrical excitation frequency provides a quantitative gas response of the gas sensing material that includes a response drift. A second electrical excitation frequency provides a baseline response of the gas sensing material based at least in part on the response drift of the quantitative gas response.

In one or more embodiments of the inventive subject matter described herein, the sensing material is a metal oxide, an inorganic material, a composite material, an organic material, a polymeric material, a nanomaterial, or the like. The sensor systems and methods described herein utilize the sensor operation methodology and hardware condition when in one of the operational states of the sensor system, the sensor system is not responding to the gases of interest but is quantitatively affected by sensor drift. For example, certain sensor operating parameters, upon exposure to gases, are not affected by these gases. The operating parameters can be used to correct the sensor response drift. For example, when measuring the MOS sensor in an AC domain, certain optimal frequencies correct sensor response drift when the sensor is in an operating mode without turning the sensor off or modulating the temperature of the sensor. Other frequencies do not provide such correction capabilities. At least one technical effect of the various embodiments herein can provide for correction of gas sensor response drift without requiring a calibration gas, without requiring removal of the sensor from the sensor system, and without requiring powering off the sensor.

Figure 1:
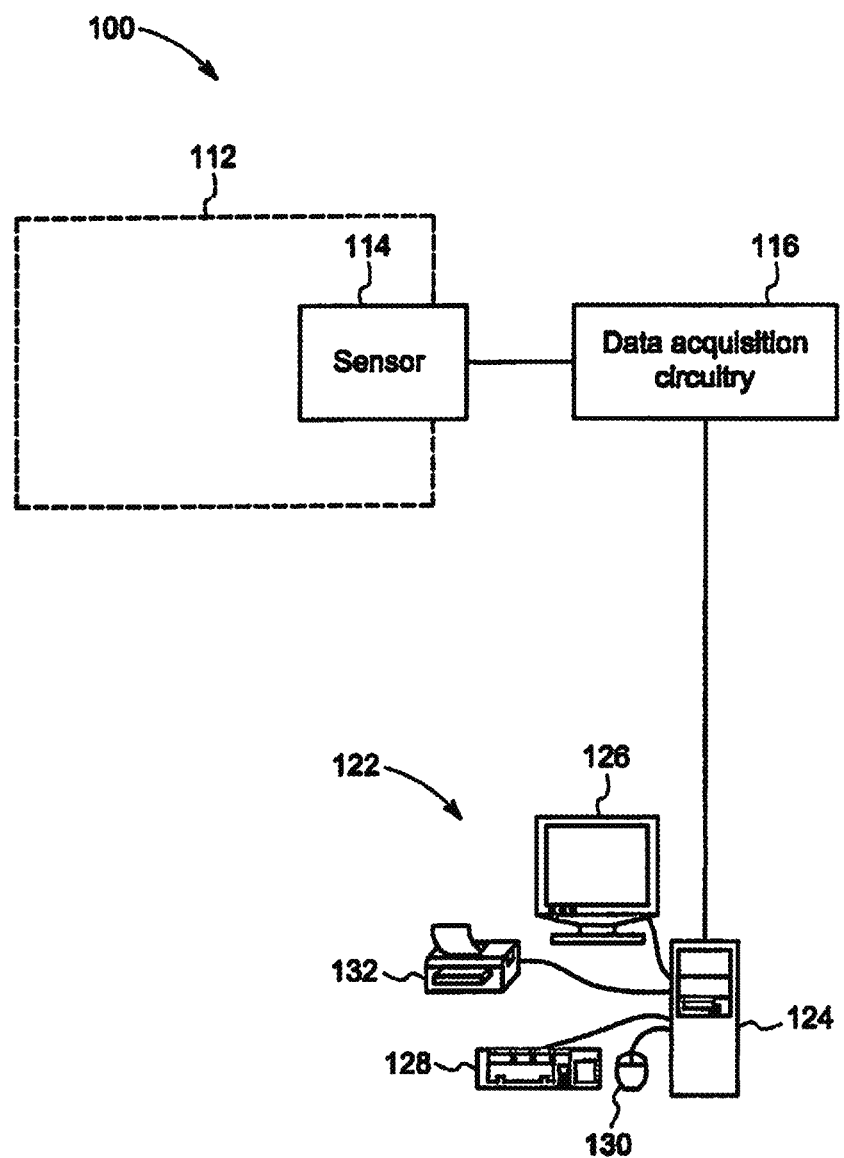
FIG. 1 illustrates one embodiment of a gas sensor system in accordance with one embodiment.

FIG. 1 illustrates one embodiment of a gas sensor system 100. The system 100 examines a fluid in contact with the system 100. The fluid may be a gas, a liquid, a gas-liquid mixture, a solid, particles or particulate matter, or the like, containing one or more analyte gases therein. The fluid may be transformer oil or any insulating fluid of an electrical transformer that is installed and/or disposed of below a ground level, above the ground level, near to the ground level, or any other position. In another embodiment, the fluid may be a gas or fuel, such as a hydrocarbon-based fuel. One example of the fluid is natural gas that is supplied to a powered system (e.g., a vehicle, or a stationary generator set) for consumption. Other examples of such a fluid can include gasoline, diesel fuel, jet fuel or kerosene, bio-fuels, petrodiesel-biodiesel fuel blends, natural gas (liquid or compressed), and fuel oils. Another example of the fluid is indoor or outdoor ambient air. Another example of the fluid is air at an industrial, residential, military, construction, urban, and any other known site. Another example of the fluid is ambient air with relatively small concentrations of hydrocarbons and/or other pollutants. Another example of the fluid is at least one gas dissolved in an industrial liquid such as transformer oil, bioprocess media, fermentation media, wastewater, and any other. Another example of the fluid is the at least one gas dissolved in a consumer liquid such as milk, non-alcoholic beverages, alcoholic beverages, cosmetics, and any other. Another example of the fluid is at least one gas dissolved in a body liquid such as blood, sweat, tears, saliva, urine, and any other.

The system 100 may include a fluid reservoir 112 for holding the fluid and one multivariable gas sensor 114 at least partially disposed in, on, or within the fluid reservoir 112. Alternatively, the sensor 114 may be set in a flow path of the fluid outside of the reservoir 112, such as coupled to in-line connectors in fluid communication with the fluid reservoir that define a flow path. The multivariable sensor may be a sensor and/or sensor system that has at least two or more outputs that are substantially independent of each other output. The fluid reservoir 112 may be in a form of a vessel with controlled volume or in a form of an open area such as an indoor facility (e.g., a room, a hall, a house, a school, a hospital, or the like), or in the form of an outdoor facility (e.g., a stadium, a gas-production site, a confined space, a seashore, a forest, or the like). In one embodiment, the sensor 114 may provide continuous monitoring of the fluid within the reservoir or flow path. In one or more embodiments, the sensor 114 may be an impedance gas sensor, a photonic sensor, an electronic sensor, a hybrid sensor, or another type of sensor. Optionally, the multivariable gas sensor may be a sensor array.

The sensor 114 may detect characteristics or properties of the fluid via a resonant or non-resonant impedance spectral response. One or more of the inductor-capacitor-resistor resonant circuits (LCR resonators) may measure the resonant impedance spectral response of the sensor. A non-resonant impedance spectral response is measured when the circuit does not contain an inductor. The resonant or non-resonant impedance spectrum of the sensor 114 in proximity to the fluid varies based on sample composition and/or components and/or temperature. The measured resonant or non-resonant impedance values Z' (which may be the real part of impedance, Zre) and Z" (which may be the imaginary part of impedance, Zim) reflect the response of the sensor 114 to the fluid.

Measurements at selected electrical excitation frequencies of a gas sensing material can be performed of the real part and/or of the imaginary part of the impedance response of the sensing material. The measurements of the real part and/or of the imaginary part of the impedance response of the sensing material can be performed at the shoulder of the dielectric relaxation peak of the impedance spectrum. These measurements can be called dielectric excitation measurements.

Other embodiments of the inventive subject matter described herein include other designs of sensors besides resonant and non-resonant impedance sensors. Other sensors can be capacitor sensors, electro-mechanical resonator sensors (e.g., tuning forks, cantilever sensors, acoustic device sensors), thermal sensors, optical sensors, acoustic sensors, photoacoustic sensors, near-infrared sensors, ultraviolet sensors, infrared sensors, visible light sensors, fiber-optic sensors, reflection sensors, multivariable sensors, or single-output sensors. The sensor may generate electrical or optical stimuli in response to measured gas in transformer oil or in isolating fluid. The insulating fluid of an electrical transformer may be insulating oil, mineral oil, synthetic oil, vegetable oil, and any other appropriate insulating fluid.

An electrical field may be applied to a sensing material or sensing film of the sensor 114 via electrodes. The distance between the electrodes and the electrodes geometry as well as the applied periodic voltage to the electrodes, may define the magnitude of the electric field applied to the sensor 114 (e.g., to the sensing material or film). The electrodes may be in direct contact with the sensing material. For example, the sensor 114 may be a combination of a sensing region and associated circuits and/or the sensing region may be coated with the sensing material. The sensing material may be semiconductor material or metal oxide material.

Suitable sensors may include single use or multi-use sensors. A suitable multi-use sensor may be a re-usable sensor that may be used during the lifetime of a system in which it may be incorporated into. In one embodiment, the sensor may be a single use sensor that may be used during all or part of a reaction or process.

Data from the sensor 114 may be acquired via data acquisition circuitry 116, which may be associated with the sensor or which may be associated with a control system, such as a controller or workstation 122 including data processing circuitry, where additional processing and analysis may be performed. The controller or workstation 122 may include one or more wireless or wired components, and may also communicate with the other components of the system 100. Suitable communication models include wireless or wired. At least one suitable wireless model includes radio frequency devices, such as radio frequency identification (RFID) wireless communications. Other wireless communication modalities may be used based on application specific parameters. Nonlimiting examples include Bluetooth, Wi-Fi, 3G, 4G, 5G, and others. For example, where there may be electromagnetic field (EMF) interference, certain modalities may work where others may not. The data acquisition circuitry 116 optionally can be disposed within the sensor 114. Other suitable locations may include disposition being within the workstation 122. Further, the workstation 122 can be replaced with a control system of the whole process where the sensor and its data acquisition circuitry may be connected to the control system of process.

The data acquisition circuitry 116 may be in the form of a sensor reader, which may be configured to communicate wirelessly or wired with the fluid reservoir 112 and/or the workstation 122. For example, the sensor reader may be a battery-operated device and/or may be powered using energy available from the main control system or by using harvesting of energy from ambient sources (light, vibration, heat, or electromagnetic energy). The data acquisition circuitry is an impedance analyzer that may provide scanning capability to measure sensor impedance across a predetermined frequency range, for example from 0.001 Hz to 10 GHz, from 0.1 Hz to 1 GHz, from 1 Hz to 100 MHZ, from 10 Hz to 10 MHz, or from 1000 Hz to 100 kHz. An impedance analyzer may provide capability to measure sensor impedance at discrete predetermined frequencies, for example at 1 Hz, 10 Hz, 100 Hz, 1 kHz, 10 kHz, 100 kHz, 1 MHz, 10 MHz, or 100 MHz.

Additionally, the data acquisition circuitry may receive data from one or more sensors 114 (e.g., multiple sensors positioned at different locations in or around the fluid reservoir). The data may be stored in short term and/or long-term memory storage devices, such as archiving communication systems, which may be located within or remote from the system and/or reconstructed and displayed for an operator, such as at the operator workstation. The sensors 114 may be positioned on or in oil fluid reservoirs, associated piping components, connectors, flow-through components, and any other relevant process components. The data acquisition circuitry 116 may include one or more processors for analyzing the data received from the sensor 114. For example, the one or more processors may be one or more computer processors, controllers (e.g., microcontrollers), or other logic-based devices that perform operations based on one or more sets of instructions (e.g., software). The instructions on which the one or more processors operate may be stored on a tangible and non-transitory computer readable storage medium, such as a memory device. The memory device may include a hard drive, a flash drive, RAM, ROM, EEPROM, and/or the like. Alternatively, one or more of the sets of instructions that direct operations of the one or more processors may be hard-wired into the logic of the one or more processors, such as by being hard-wired logic formed and/or stored in the hardware of the one or more processors.

In addition to displaying the data, the operator workstation 122 may control the above-described operations and functions of the system 100. The operator workstation 122 may include one or more processor-based components, such as general purpose or application-specific computers or processors 124. In addition to the processor-based components, the computer may include various memory and/or storage components including magnetic and optical mass storage devices, internal memory, such as RAM chips. The memory and/or storage components may be used for storing programs and routines for performing the techniques described herein that may be executed by the operator workstation 122 or by associated components of the system 100. Alternatively, the programs and routines may be stored on a computer accessible storage and/or memory remote from the operator workstation 122 but accessible by network and/or communication interfaces present on the computer 124. The computer 124 may also comprise various input/output (I/O) interfaces, as well as various network or communication interfaces. The various I/O interfaces may allow communication with user interface devices, such as a display 126, keyboard 128, electronic mouse 130, and printer 132, that may be used for viewing and inputting configuration information and/or for operating the imaging system. Other devices, not shown, may be useful for interfacing, such as touchpads, heads up displays, microphones, and the like. The various network and communication interfaces may allow connection to both local and wide area intranets and storage networks as well as the Internet. The various I/O and communication interfaces may utilize wires, lines, or suitable wireless interfaces, as appropriate or desired.

Figure 2:
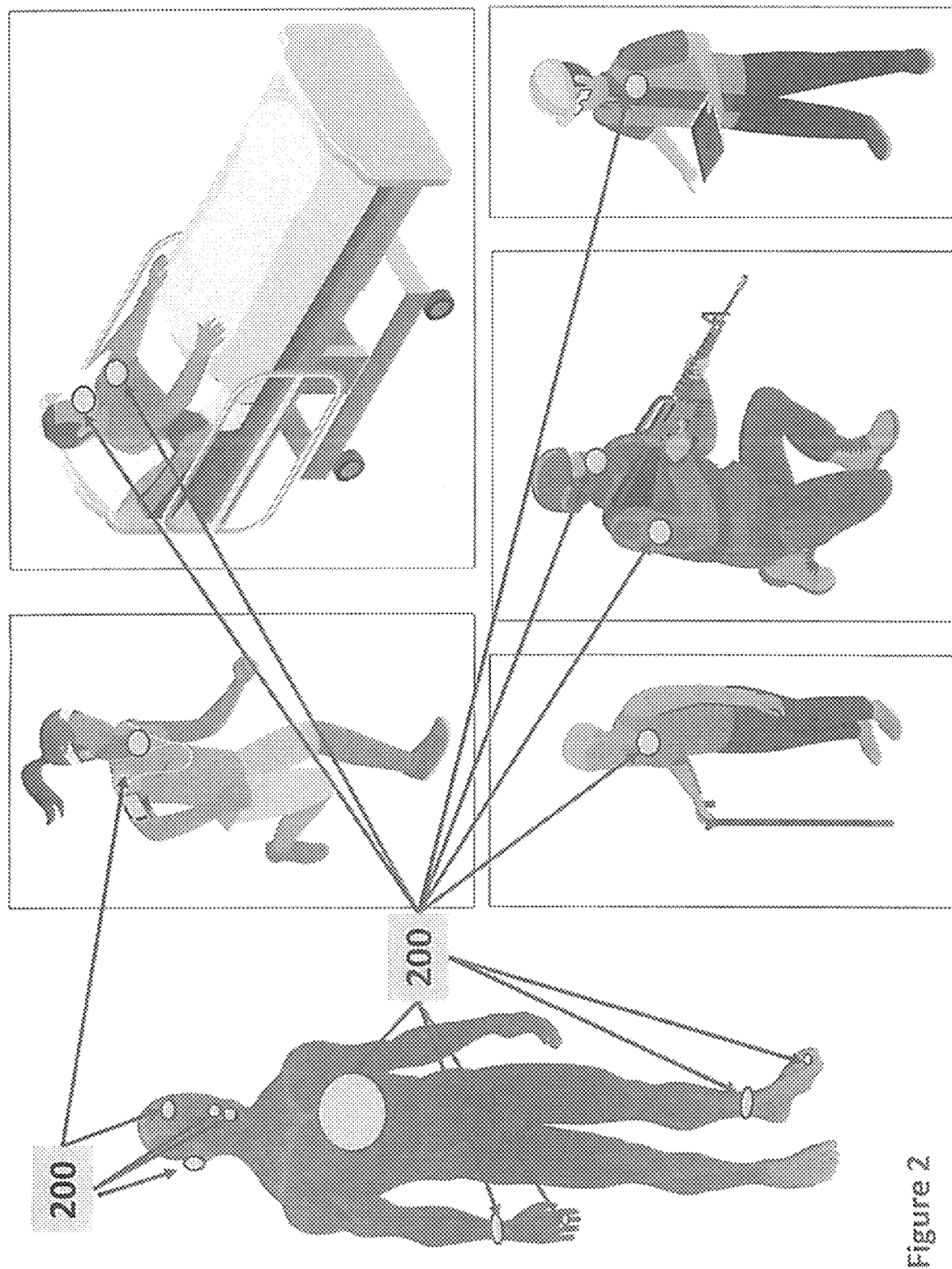
FIG. 2 illustrates exemplary positions of a wearable sensor system in accordance with one embodiment.

In one or more embodiments, the sensor system 100 may be a wearable sensor system, may be held within a wearable and/or non-wearable transferable object (e.g., a frame of military or industrial eyeglasses), or the like. The wearable device may be worn by a subject, such as a human or animal, may be removably coupled or integrated with an article worn by a subject (e.g., a shirt, pants, safety vest, personal protection clothes, eyeglasses, hat, safety helmet, hearing device, or the like), or may be any alternative device that may be transferable such that sensor can be moved between different positions, may be stationary or substantially stationary, or the like. FIG. 2 illustrates exemplary positions 200 of different wearable sensors 114. In the illustrated embodiment of FIG. 2, the subject is a human subject, however the subject may be a mammal subject, a plant subject, or the like.

Figure 3:
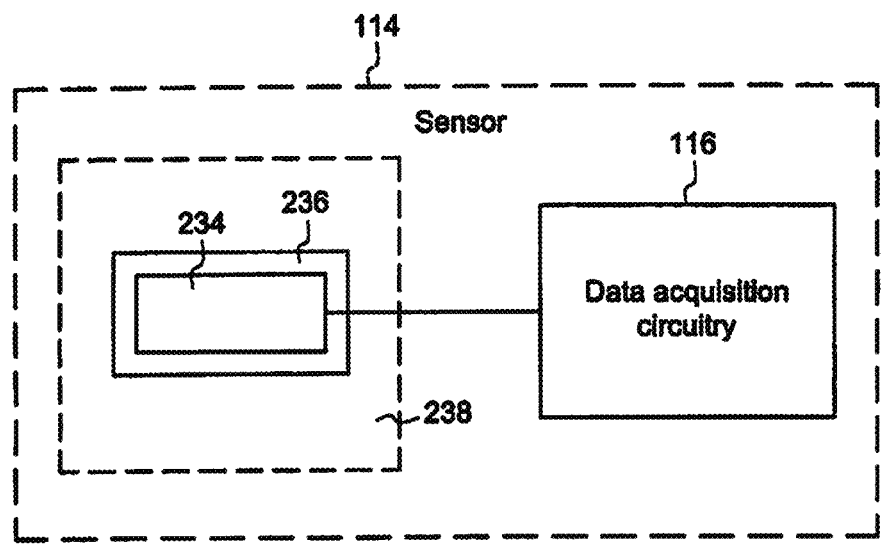
FIG. 3 illustrates a non-limiting example of a design of a sensor shown in FIG. 1 in accordance with one embodiment.

FIG. 3 illustrates a non-limiting example of a design of the sensor 114. A sensing electrode structure 234 of the sensor 114 may be connected to the data acquisition circuitry 116. The sensing electrode structure 234 can be coated with a sensing film or sensing material 236. The sensing electrode structure 234, with the sensing film 236, forms a sensing region circuit 238. The sensing electrode structure 234, with the sensing film 236 that forms the sensing region circuit 238, may operationally contact a fluid. The fluid contains the one or more analyte gases therein.

Suitable interdigital electrode structures for probing a fluid sample include two- and four-electrode structures. Suitable materials for electrodes include stainless steel, platinum, gold, noble metals, and others. Suitable materials of a substrate may include silicon dioxide, silicon nitride, alumina, ceramics, and others. Suitable examples of sensing materials or sensing films include a metal oxide material, a composite material, semiconducting materials, n-type semiconducting materials, p-type semiconducting materials, nanocomposite materials, inorganic materials, organic materials, polymeric materials, formulated materials, any known sensing material, or the like. Suitable electrodes may be formed using metal etching, screen-printing, ink-jet-printing, and mask-based metal deposition techniques. The thickness of fabricated electrodes on the substrates may be in the range from about 10 nanometers to about 1000 micrometers. The materials for the interdigital electrode structures, substrate, sensing layer, and electrode formation methods may be selected based at least in pan on the application specific parameters.

Figure 4:
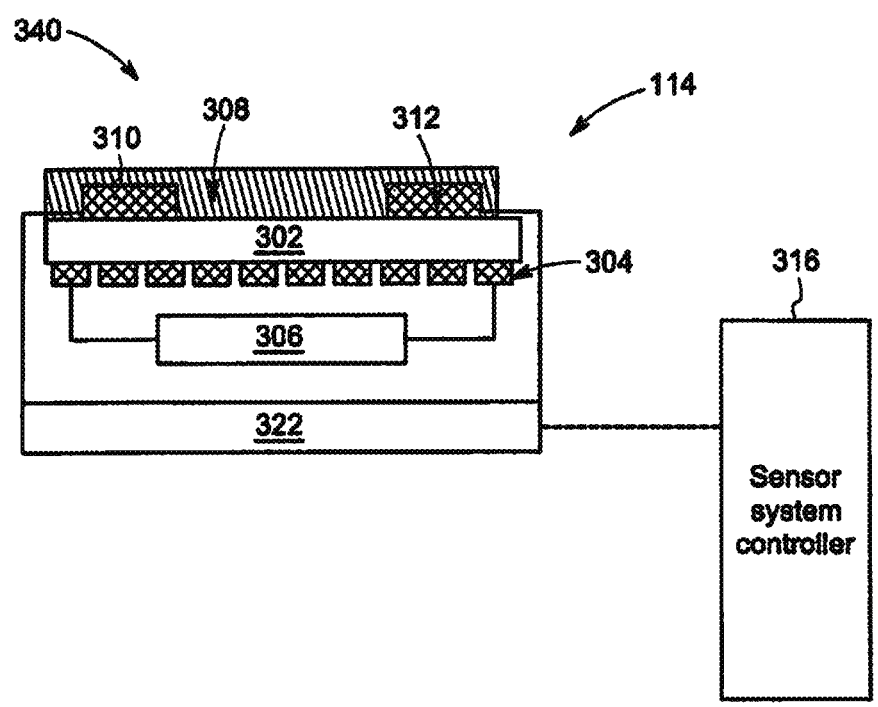
FIG. 4 illustrates one embodiment of a sensor in accordance with one embodiment.

FIG. 4 illustrates one embodiment of the multivariable gas sensor 114. The sensor 114 may represent another version of the sensors or sensing systems described herein. The sensor 114 includes a gas sensing element 340 having a substrate 302, such as a dielectric material, a gas sensing film or gas sensing material 308 that is coupled to the substrate 302, and electrodes 310, 312. The gas sensing material 308 is exposed to, in direct contact with, in indirect contact with, or the like, at least one analyte gas. One or several heating elements 304, such as high resistance bodies, are coupled to a different side of the substrate 302 relative to the sensing material 308. The heating elements 304 receive electric current from a heater controller 306, which represents hardware circuitry that conducts the heater current or voltage to the heating elements 304 to heat the substrate 302 and to heat the sensing film or gas sensing material 308 that is coupled to another side of the substrate 302. For example, in one or more embodiments of the inventive subject matter described herein, the gas sensing material 308 utilizes a metal oxide sensing film. The gas sensing material 308 can include one or more materials deposited onto the substrate 302 to perform a function of predictably and reproducibly affecting the impedance sensor response upon interaction with the environment. For example, a metal oxide, such as $SnO_2$, may be deposited as the gas sensing material 308.

The electrodes 310, 312 are coupled with and/or disposed in the gas sensing material 308 and are connected with the substrate 302 in the illustrated embodiment. The electrodes 310, 312 are conductive bodies that are conductively coupled with an impedance detector system 322. Optionally, the sensing electrodes 310, 312 may be directly or indirectly conductively coupled with one or more additional systems such as, but not limited to, a resistance detector system. The impedance detector system 322 may include one or more processors that include one or more microprocessors, field programmable gate arrays, and/or integrated circuits.

In one or more embodiments, the sensing electrodes 310, 312 may be coated with a sensing material that is responsive to one or more analyte gases of interest. The one or more processors of the impedance detector system 322 also direct the sensing electrodes 310, 312 to apply the electrical stimuli at different frequencies, such as one or more different electrical excitation frequencies. The one or more processors of the impedance detector system 322 may also receive an electrical signal from the electrodes 310, 312 that represents the electrical impedance or impedance response of the gas sensing element 340 during exposure of the sensing material 308 to the fluid sample. In alternative embodiments, the impedance detector system 322 may be referred to as a frequency impedance source and detector system. The impedance detector system 322 examines the electrical impedance of the gas sensing element 340 in order to determine the presence and/or amount (e.g., concentration) of one or more analyte gases in the environment to which the sensing material 308 is exposed, as described herein. The impedance detector system 322 may provide scanning capability to measure sensor impedance responses at a single or at plural discrete frequencies. Alternatively, the impedance detector system 322 may provide capability to measure sensor impedance responses across a frequency range.

In one or more embodiments, the sensor 114 may include a resistance detector system (not shown) that includes one or more processors and can receive an electrical signal from the sensing electrodes 310, 312 that represents a resistance or a resistance response of the sensing material 308 during exposure of the sensing material 308 to the fluid sample. The resistance detector system may examine the resistance response of the gas sensing material 308 in order to determine the presence and/or amount (e.g., concentration) of one or more analyte gases in the environment in which the gas sensing material 308 is exposed. In alternative embodiments, the impedance detector system 322 and the resistance detector system may be disposed within a common housing, may include common and/or unique integrated circuits and/or circuitry that allows the system to operate as either an impedance system or a resistance detector system, or any combination therein.

A sensor system controller 316 is operably coupled with the impedance detector system 322, and optionally with the heater controller 306. The sensor system controller 316 includes one or more processors that include one or more microprocessors, field programmable gate arrays, and/or integrated circuits. The sensor system controller 316 controls the impedance detector system 322 to apply electrical stimuli to the electrodes 310, 312 for interrogation of the gas sensing material 308. The controller 316 directs the impedance detector system 322 to apply electrical stimuli at two or more different electrical excitation frequencies. For example, a first electrical stimuli may be applied at a first electrical excitation frequency, a subsequent second electrical stimuli may be applied at a different, second electrical excitation frequency, and a third electrical stimuli may be applied at a third electrical excitation frequency. The first, second, and third electrical excitation frequencies may be common or different frequencies, different frequency ranges, or the like, relative to each other electrical excitation frequency.

The sensor system controller 316 can operate in two or more different modes of operation including a gas response mode and a baseline correction mode. Optionally, the controller 316 may operate in any additional and/or alternative modes of operation. The controller 316, operating in the gas response mode of operation, can direct the electrodes 310, 312 to apply the first electrical stimuli at the first electrical excitation frequency to the gas sensing material 308. Responsive to applying the first electrical stimuli at the first electrical excitation frequency, the one or more processors of the system controller 316 receives a quantitative gas response of the gas sensing material 308 that includes a response drift. In one or more embodiments, the response drift may refer to an uncontrolled change in the sensor response that can either increase or decrease the sensor response values over a time period. The response drift may be a slow change that occurs over a predetermined amount of time, or may occur at any speed.

Operating in the gas response mode and subsequent to or substantially simultaneously as the processors of the sensor system controller 316 apply the first electrical stimuli and/or receive the quantitative response from the gas sensing element 340, the sensor system controller 316 can direct the electrodes 310, 312 to apply the second electrical stimuli at the second electrical excitation frequency to the gas sensing material 308. Responsive to applying the second electrical stimuli at the second electrical excitation frequency, the one or more processors of the system controller 316 receives a signal including a baseline response of the gas sensing material 308 that is based, at least in part, on the response drift of the quantitative gas response. The baseline or baseline response may also refer to the sensor response that is in the absence of a gas or gases of interest but rather a sensor response in the presence of a clean carrier gas. For example, the second electrical excitation frequency utilizes the response drift of the quantitative gas response of the gas sensing material 308 to move the quantitative gas response toward a target threshold of the quantitative gas response. The target threshold may be a predetermined value of the sensor response, a predetermined range of values of the sensor response, or the like.

In one or more embodiments, the gas sensor 114 may include a baseline correction controller for baseline correction of the baseline response. In one embodiment, the baseline correction controller may be contained within a common housing, structure, or the like, as the sensor system controller 316 and/or may be controlled by the same or common one or more processors of the sensor system controller 316. In an alternative embodiment, the controller for baseline correction may be a separate entity that includes one or more processors that include one or more microprocessors, field programmable gate arrays, and/or integrated circuits and is separate and distinct from the sensor system controller 316. Optionally, the sensor system controller 316 and the baseline correction controller may have any alternative configuration. Operating in the baseline correction mode, the sensor system controller 316 can correct the baseline response.

The sensor system controller 316 directs the electrodes 310, 312 to apply the first and second electrical stimuli at the first and second electrical excitation frequencies, respectively, when the gas sensor system 100 is in an operating state. For example, the gas sensor system 100 operates under normal or typical operating conditions (e.g., at a substantially constant voltage of power supply and substantially constant operating temperatures) when the system controller 316 controls operation of the impedance detector system 322, the heater controller 306, and/or any alternative system, when the gas sensor system 100 is operating, or in an operating state, on-mode, or the like. The sensor system controller 316 controls operation of the impedance detector system 322 and/or the heater controller 306 without the gas sensor system 100 changing from an operating state to a non-operating state, an off-mode, a standby-mode, a sleep-mode, or the like. When the gas sensor system 100 operates under the normal and/or typical operating conditions, the sensor system 100 can be presented to a measured environment where a gas of interest or gases of interest are expected to be present. Impedance of the gas sensor 114 is measured to determine the gas concentrations. The sensor system controller 316 is operated to select operating frequencies between the gas response mode and the baseline correction mode (e.g., the first and second electrical excitation frequencies). Such measurements can be done in a sequence (e.g., once every 10 milliseconds, once every second, once every minute), or can be done almost or substantially simultaneously relative to each other measurement. A correction is applied to the sensor output that includes the gas response to correct for the baseline drift.

In one or more embodiments, the sensor 114 may include a bank of circuits (not shown). The bank of circuits can include plural circuits that each include one or more passive electrical components. The sensor system controller 316 can direct one or more of the plural circuits to open and/or close to change the impedance of the electrical stimuli applied to the sensing material 308. Opening each of the circuits (not shown) electrically disconnects each of the circuits from the sensing electrodes 310, 312. Closing the circuits electrically connects or electrically couples the circuits with the sensing electrodes 310, 312. For example, the impedance of the sensing element 340 may be changed without changing the electrical excitation frequency of the electrical stimuli applied to the sensing electrodes 310, 312 via one or more of the plural circuits opening and/or closing. The circuits that are opening and/or closing change the electrical excitation conditions of the sensing material 308.

Figure 5:
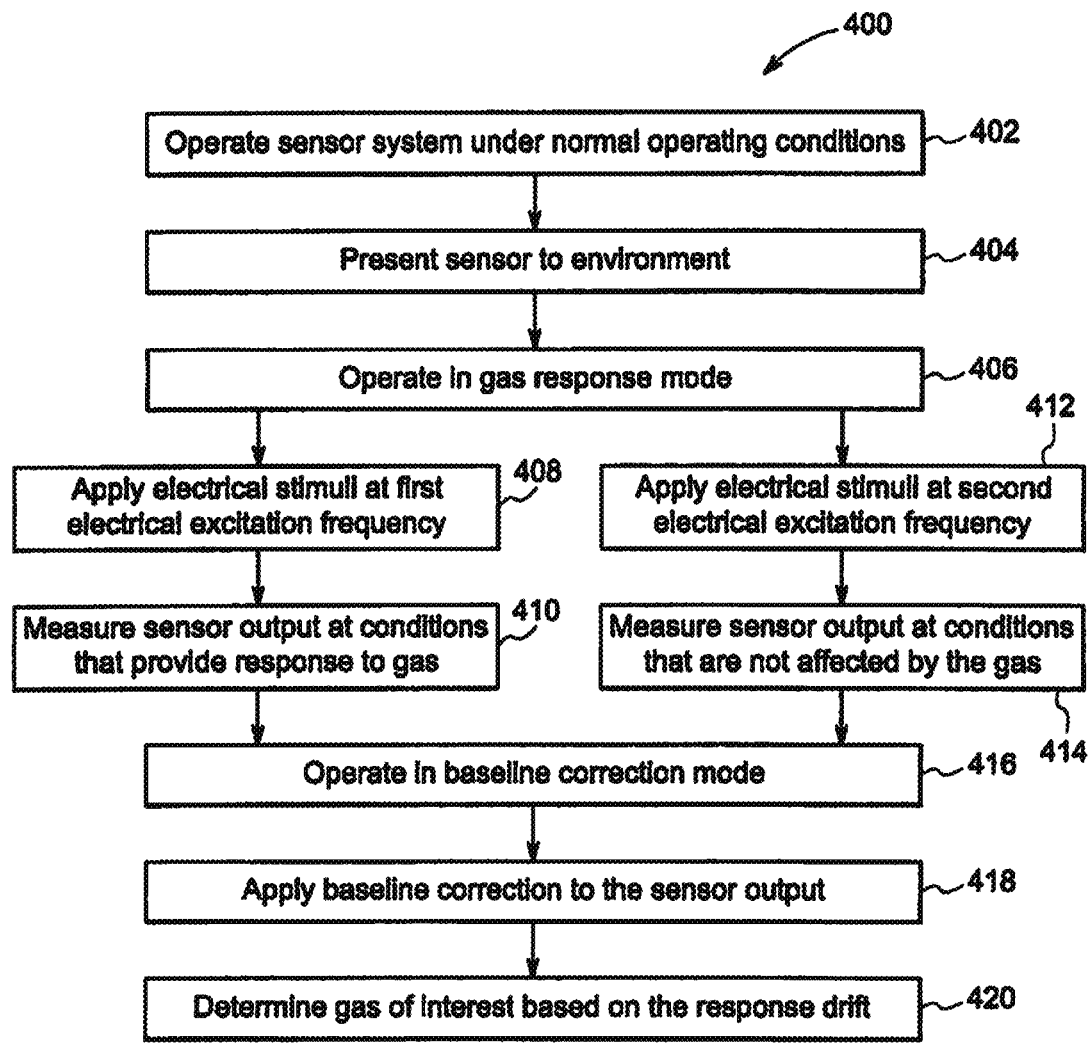
FIG. 5 illustrates a flowchart of one embodiment of a method for correcting a sensor output in accordance with one embodiment.

FIG. 5 illustrates a flowchart of one embodiment of a method 400 for correcting a sensor output in accordance with one embodiment. The method 400 can represent the operations performed by the gas sensor system 100 and/or the gas sensing element 340 described herein, or optionally can represent the operations performed by another sensing system and/or another gas sensor. For example, the method 400 can represent operations performed by the system 100 and/or the sensing element 340 under direction of one or more software applications, or optionally can represent an algorithm useful for writing such software applications. Additionally or alternatively, one or more of the steps of the method 400 may be bypassed, omitted, performed in any alternative order relative to each other step, or any combination therein.

At 402 the gas sensor system 100 is operated under normal, typical, or the like, operating conditions. As one example, the gas sensor system 100 may be operating under a predetermined substantially constant voltage of power supply, a predetermined substantially constant operating temperature, or the like. The normal operating conditions may vary or remain substantially constant between a first time operating the gas sensor system 100 and a second time operating the gas sensor system 100.

At 404, the gas sensor system 100 is presented to a measured environment where a gas or gases of interest are expected to be present. For example, the system 100 may be disposed within a residential building such as proximate a home appliance, an industrial facility having oil fluid reservoirs, associated piping components, connectors, flow-through components, an airplane, locomotive, truck, passenger car, or the like. At 406, the sensor system controller 316 of the sensor system 100 operates in a gas response mode.

At 408, the sensor system controller 316 directs the electrodes 310, 312 to apply a first electrical stimuli at a first electrical excitation frequency to the sensing material 308. The first electrical excitation frequency may be a discrete frequency, such as for example at 1 Hz, 10 Hz, 100 Hz, 1 kHz, 10 kHz, 100 kHz, 1 MHz, 10 MHz, 100 MHz, greater than 100 MHz, or the like. Optionally, the first electrical excitation frequency may be a frequency range, such as, from 0.001 Hz to 10 GHz, from 0.1 Hz to 1 GHz, from 1 Hz to 100 MHZ, from 10 Hz to 10 MHz, or from 1000 Hz to 100 kHz.

At 410, responsive to the electrodes 310, 312 applying the first electrical stimuli to the gas sensing material 308, the sensor system controller 316 receives a sensor output at conditions that provide response to the gas of interest or gases of interest. The sensor output may be a quantitative gas response, such as a sensor impedance response that may include a response drift.

At 412, the sensor system controller 316 directs the electrodes 310, 312 to apply a second electrical stimuli at a second electrical excitation frequency to the sensing material 308 that is different than the first electrical excitation frequency. The second electrical excitation frequency may be a discrete frequency, such as for example at 1 Hz, 10 Hz, 100 Hz, 1 kHz, 10 kHz, 100 kHz, 1 MHz, 10 MHz, 100 MHz, greater than 100 MHz, or the like. Optionally, the second electrical excitation frequency may be a frequency range, such as, from 0.001 Hz to 10 GHz, from 0.1 Hz to 1 GHz, from 1 Hz to 100 MHZ, from 10 Hz to 10 MHz, or from 1000 Hz to 100 kHz.

In one or more embodiments, the sensor system controller 316 may direct the electrodes 310, 312 to apply the first and second electrical stimuli to the gas sensing material 308 in a rapid sequence (e.g., separated by a time of about 10 milliseconds, 1 second, 1 minute, or the like). Optionally, the first and second electrical stimuli may be applied substantially simultaneously.

At 414, responsive to the electrodes 310, 312 applying the second electrical stimuli to the gas sensing material 308, the sensor system controller 316 receives a sensor output at conditions that are not affected by the gas of interest or gases of interest. The sensor output may be a baseline response that is based, at least in part, on the response drift of the quantitative gas response.

Figure 6:
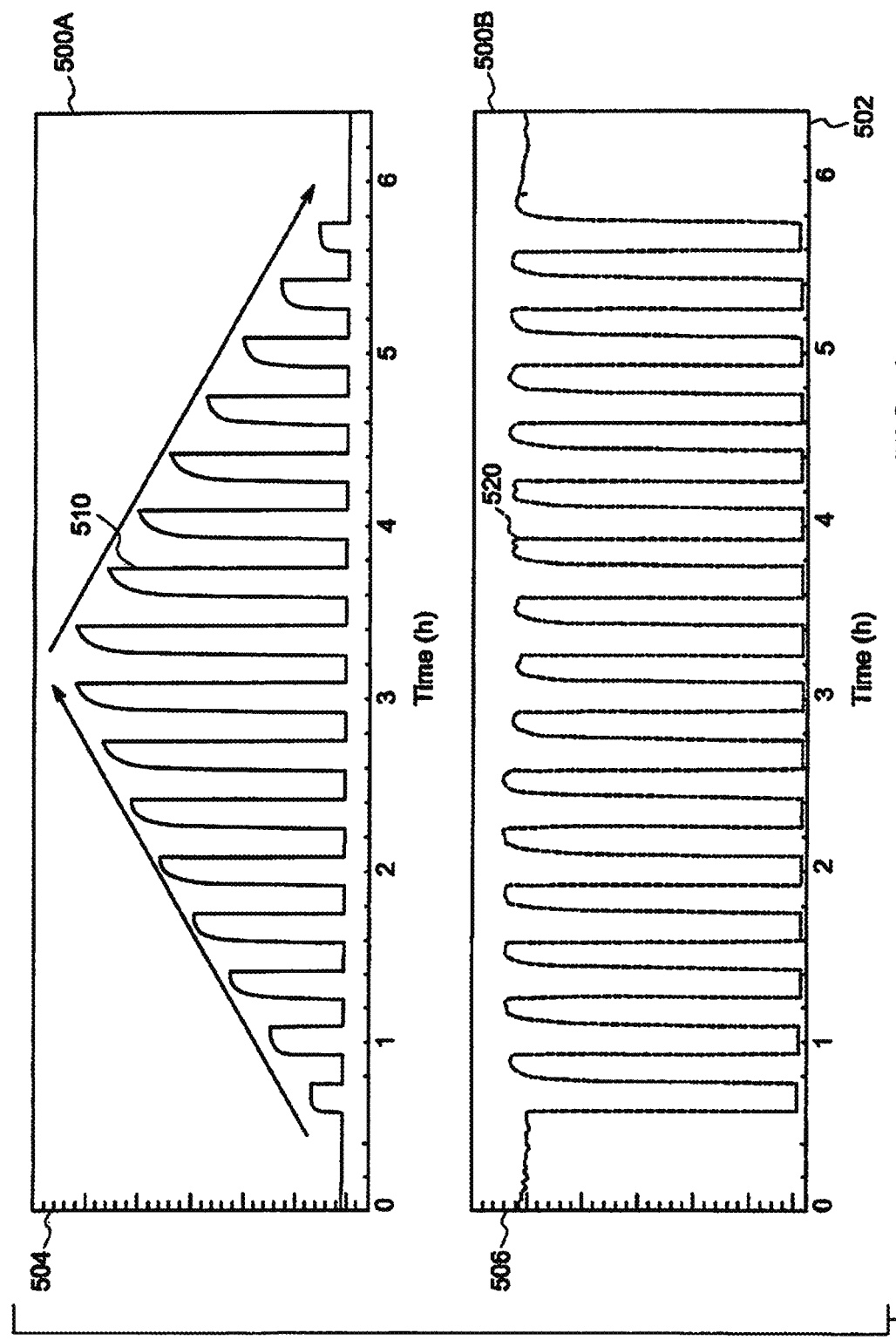
FIG. 6 depicts a graphical illustration of a sensor impedance response and a sensor resistance response in accordance with one embodiment.

FIG. 6 illustrates a graphical illustration of a sensor impedance response 500A and a sensor resistance response 500B in accordance with one embodiment. The graphs 500A, 500B include a common horizontal axis 502 representative of time. The graph 500A includes a vertical axis 504 representative of increasing values of impedance, and the graph 500B includes a vertical axis 506 representative of increasing values of resistance. As one example, the sensor 114 of the gas sensor system 100 is exposed to methane gas (CH4) for about six (6) hours of operation of the gas sensor system 100 in the range of gas concentrations up to about 1% by volume. Graph 500A illustrates the sensor impedance response 510 that provides a substantially linear response as a function of gas concentration over time. Alternatively, graph 500B illustrates the sensor resistance response 520 that saturates over time and does not allow quantitation of the methane gas.

Figure 7:
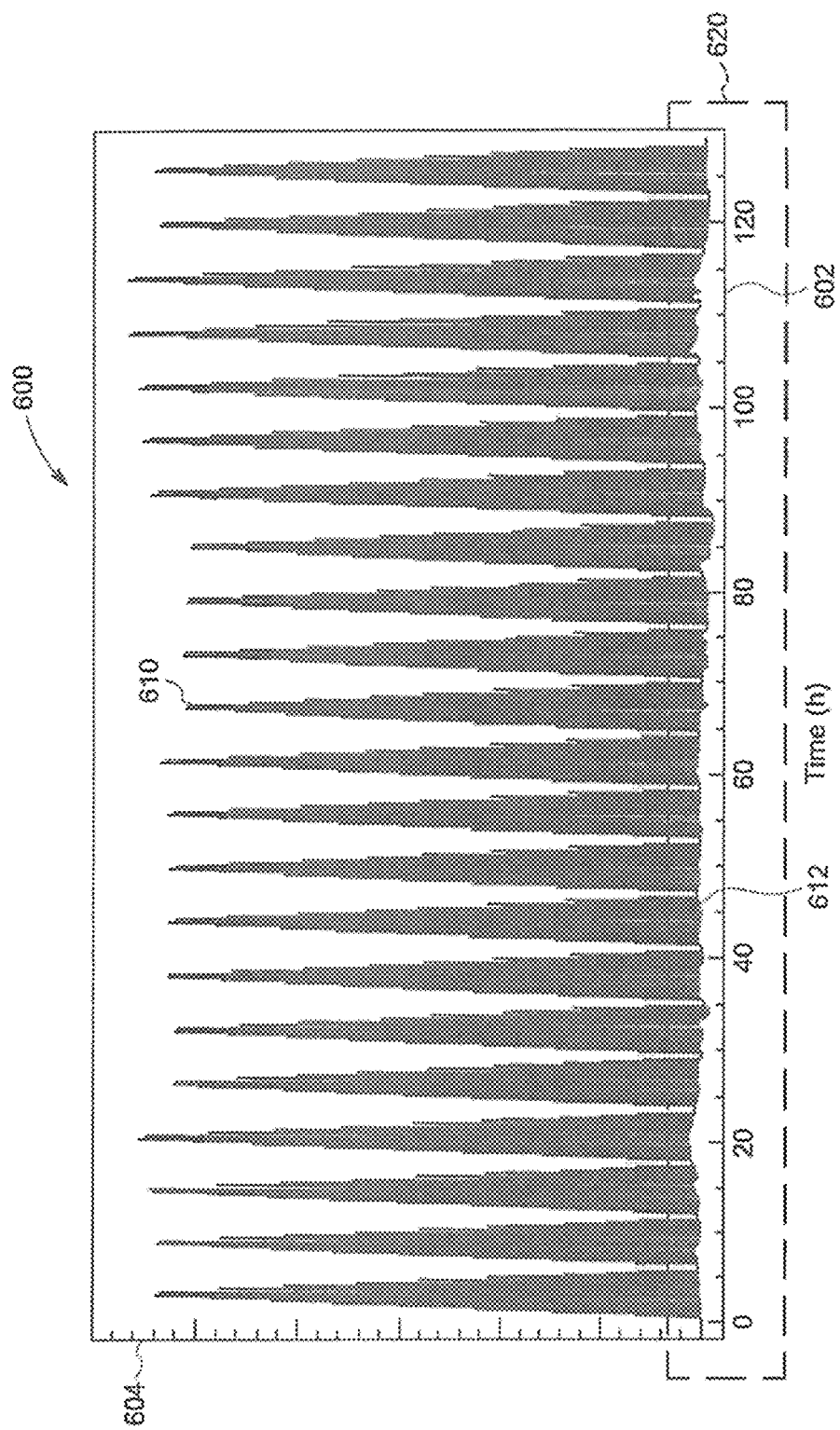
FIG. 7 depicts a graphical illustration of a sensor response to periodic exposures to methane in accordance with one embodiment.

Alternatively, FIG. 7 illustrates a graphical illustration of a graph 600 of a sensor response to periodic exposures to methane in accordance with one embodiment. The graph 600 includes a horizontal axis 602 representative of time, and a vertical axis 604 representative of increasing values of impedance. The graph 600 illustrates a first sensor response 610 to periodic exposures to methane gas (CH4) for about 130 hours of the test. In the illustrated embodiment, the sensor 114 did not degrade the sensor response after plural cycles of exposure to methane. Additionally, the first sensor response 610 includes a response drift 612 that is observed over the 130 hour time period of the test. The response drift 612 varies, changes, fluctuates, or the like, over the 130 hour time period of the test. For example, the response drift 612 illustrates an unstable baseline of the first sensor response 610.

Figure 8:
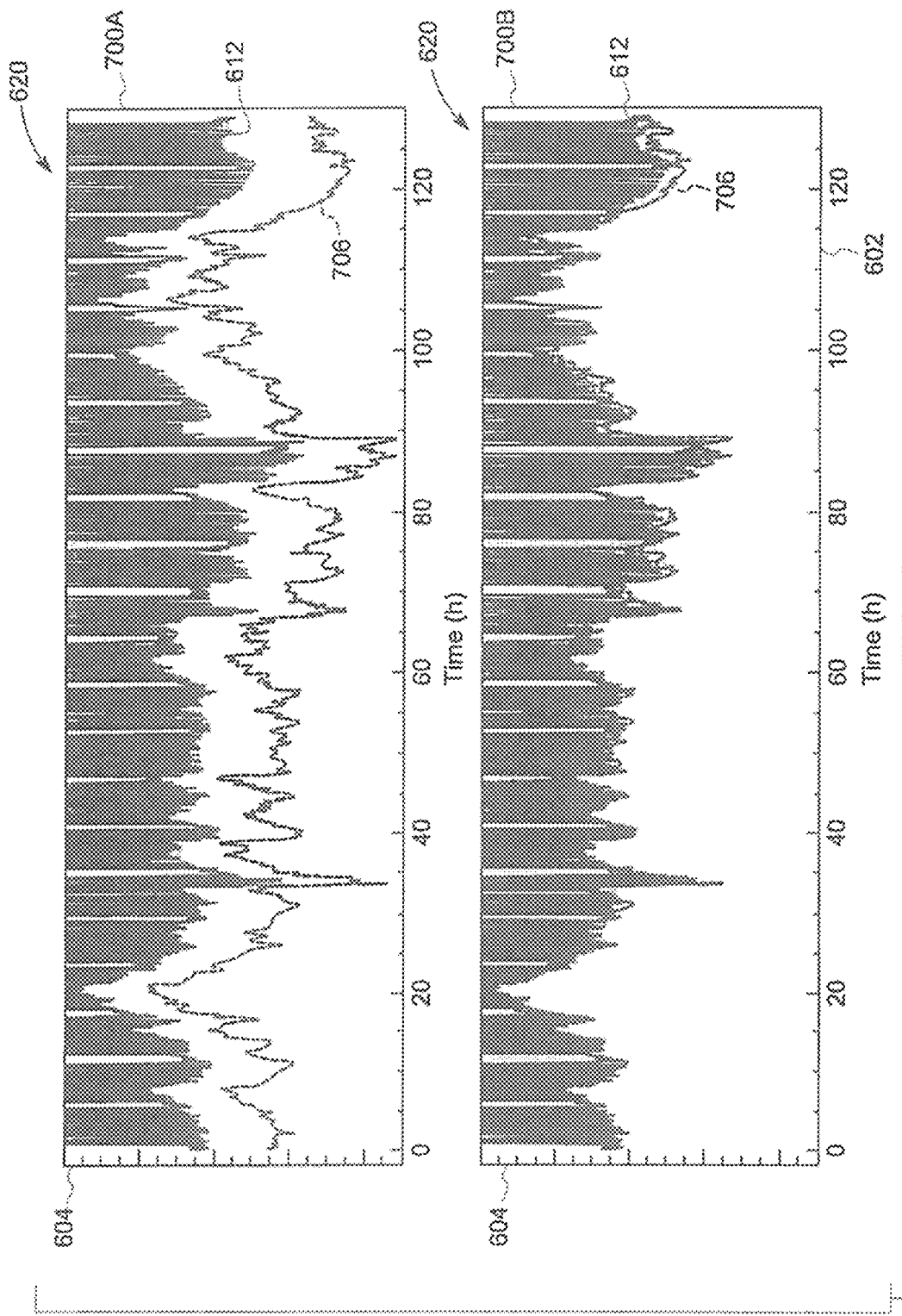
FIG. 8 depicts a graphical magnified illustration of the sensor response shown in FIG. 7 in accordance with one embodiment.

FIG. 8 illustrates a graphical magnified illustration of section 620 of the first sensor response 610 shown in FIG. 7 in accordance with one embodiment. Graphs 700A and 700B include the common horizontal axis 602 representative of time, and the common vertical axis 604 representative of increasing values of impedance. Illustrated in graph 700A, the first sensor response 610 includes a response drift 612 over the 130 hour time period of the test. The graph 700A also includes a second sensor response 706 of the sensor 114 that did not produce a response to the gas of interest, but was affected by the response drift. For example, the first sensor response 610 may represent the sensor output of the sensor responsive to the electrode 310, 312 applying the first electrical stimuli to the gas sensing material 308 that is representative of the quantitative gas response, and the second sensor response 706 may represent the sensor output of the sensor responsive to the electrodes 310, 312 applying the second electrical stimuli to the gas sensing material 308, that is based, at least in part, on the response drift of the quantitative gas response (e.g., the response drift 612). For example, the quantitative gas response sensor output responsive to the first electrical stimuli applied at the first electrical excitation frequency (e.g., the first sensor response 610) includes the response drift 612 provides a response to the gas or gases of interest. The baseline response sensor output responsive to the second electrical stimuli applied at the second electrical excitation frequency (e.g., the second sensor response 706) provides a response to conditions not affected by the gas or gases of interest.

The graph 700A illustrates the first and second sensor responses 610, 706 separated from each other response for clarity. The graph 700B illustrates the two sensor responses 610, 706 more closely overlaid relative to the graph 700A to illustrate the similarity between the response drift 612 and the second sensor response 706 illustrating the baseline response.

Returning to the flowchart of the method 400, at 416, the sensor system controller 316 changes from operating in the gas response mode to the baseline correction mode. Optionally, the gas sensor 114 may include a baseline correction controller for baseline correction of the baseline response that is separate from the sensor system controller 316. At 418, the sensor system controller 316 applies a baseline correction to the first and second sensor responses 610, 706 to determine a difference between the response drift 612 and the second sensor response 706 (e.g., the baseline response). The sensor system controller 316 may use subtraction or any other mathematical manipulation to determine a difference between the response drift 612 and the baseline response 706. The two different sensor outputs (e.g., the first sensor response 610 and the second sensor response 706) can be mathematically manipulated relative to each other (e.g., compared, subtracted, or the like) to determine a difference between the two sensor outputs and to correct the second sensor response 706 (e.g., the baseline response). Additionally, the sensor system controller 316 can determine an amount of the response drift 612 at one or more different moments in time of the quantitative gas response (e.g., the first sensor response 610). Additionally or alternatively, the sensor system controller can determine a difference between the quantitative gas response, including the response drift 612, and the baseline response 706. In one or more embodiments, the sensor system controller can control one or more of the circuits to change the impedance of the electrical stimuli applied to the sensing material 308. For example, the sensor system controller may control one or more of the plural circuits to apply the baseline correction to the first and second sensor responses without changing the electrical excitation frequency of the electrical stimuli applied to the sensing electrodes.

At 420, a gas or gases of interest are determined based on the response drift of the quantitative gas response. For example, the gas of interest may be determined based on the first sensor response 610 that provides an impedance response to the gas of interest and based on the second sensor response 706 that is not affected by the gas of interest but was affected only by the response drift 612.

The gas sensor system 100 may also improve a limit of detection (LOD) of the sensor 114. The limit of detection may represent the smallest gas concentration that can be detected at a certain confidence, such as at a 3σ level. The limit of detection of a gas of interest can be calculated at a signal-to-noise ratio (SNR) of three from the sensor response S at the smallest measured gas concentration and the measured sensor baseline noise a based on the following equation:

$$LOD = SNR \times \sigma \times [gas]/S \qquad \text{Eq. 1}$$

Figure 9:
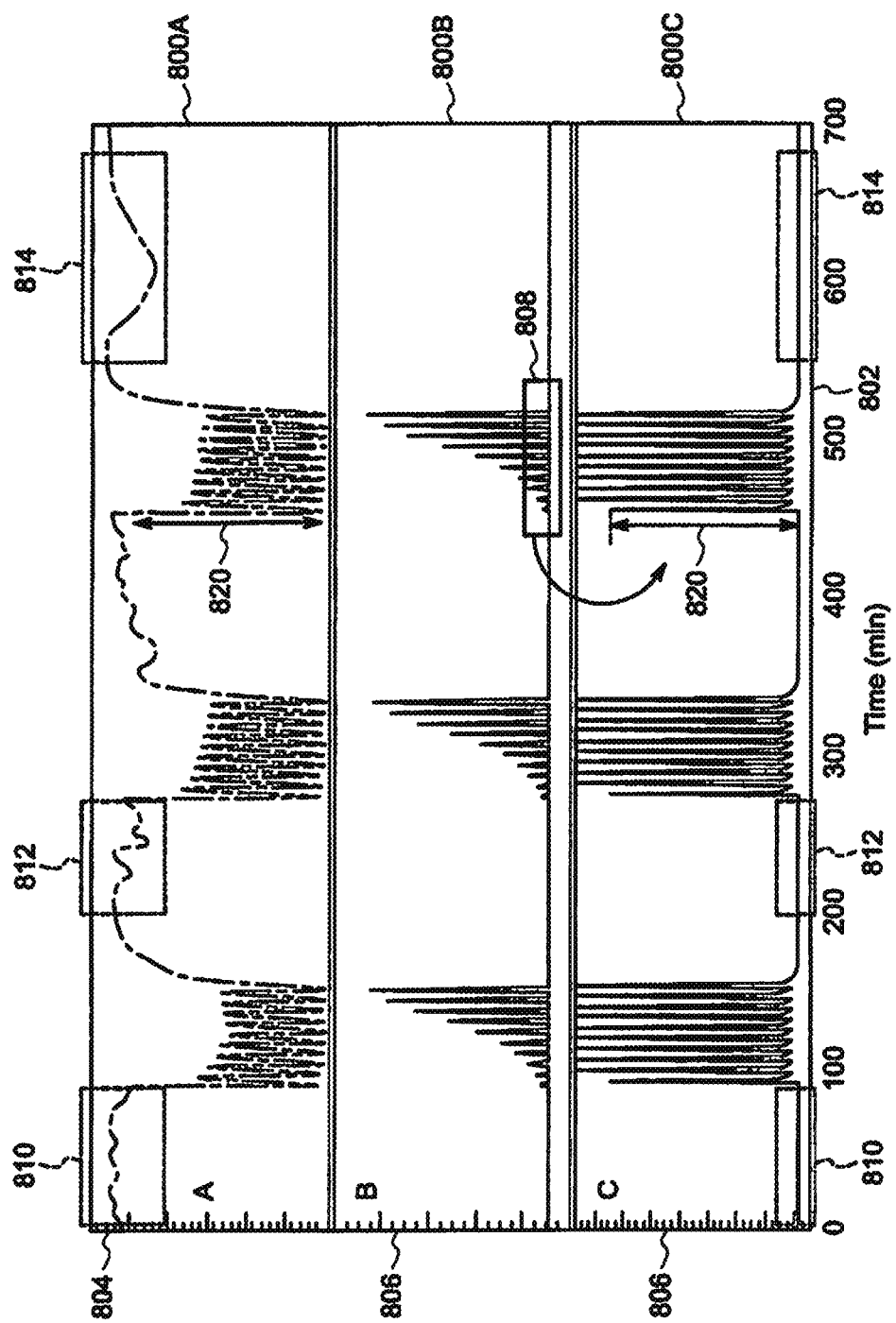
FIG. 9 depicts graphical illustrations of resistance changes and impedance changes of a hydrogen sensor response to exposure of hydrogen gas in accordance with one embodiment.

FIG. 9 illustrates graphical illustrations of resistance changes and impedance changes of a sensor response to exposure of hydrogen gas in accordance with one embodiment. Graph 800A illustrates change in resistance of the sensor 114, graph 800B illustrates a change in impedance of the sensor 114, and graph 800C illustrates a magnified view of the change in impedance of the sensor illustrated in graph 800B. The graphs 800A, 800B, 800C share a common horizontal axis 802 representative of time. Graph 800A includes a vertical axis 804 representative of increasing values of resistance, and graphs 800B, 800C share a vertical axis 806 representative of increasing values of impedance.

In the illustrated embodiment of FIG. 9, the sensor 114 was exposed to varying concentrations of hydrogen gas over a test time of about 700 minutes. Graph 800A illustrates the resistance response when the sensor 114 was operating in a resistance mode of operation, and the graphs 800B, 800C illustrate the impedance response when the sensor 114 was operating in an impedance mode of operation. Exposures were performed to hydrogen gas concentrations ranging up to 500 parts per million (ppm) in steps 820 of 50 ppm. The resistance change, illustrated in graph 800A, of the sensor 114 includes fluctuation of baselines 810, 812, 814 in addition to the response to the hydrogen gas. Alternatively, the impedance change, illustrated in graphs 800B and 800C include less contributions of fluctuations of the baselines 810, 812, 814 relative to the resistance measurements illustrated in graph 800A.

Figure 10:
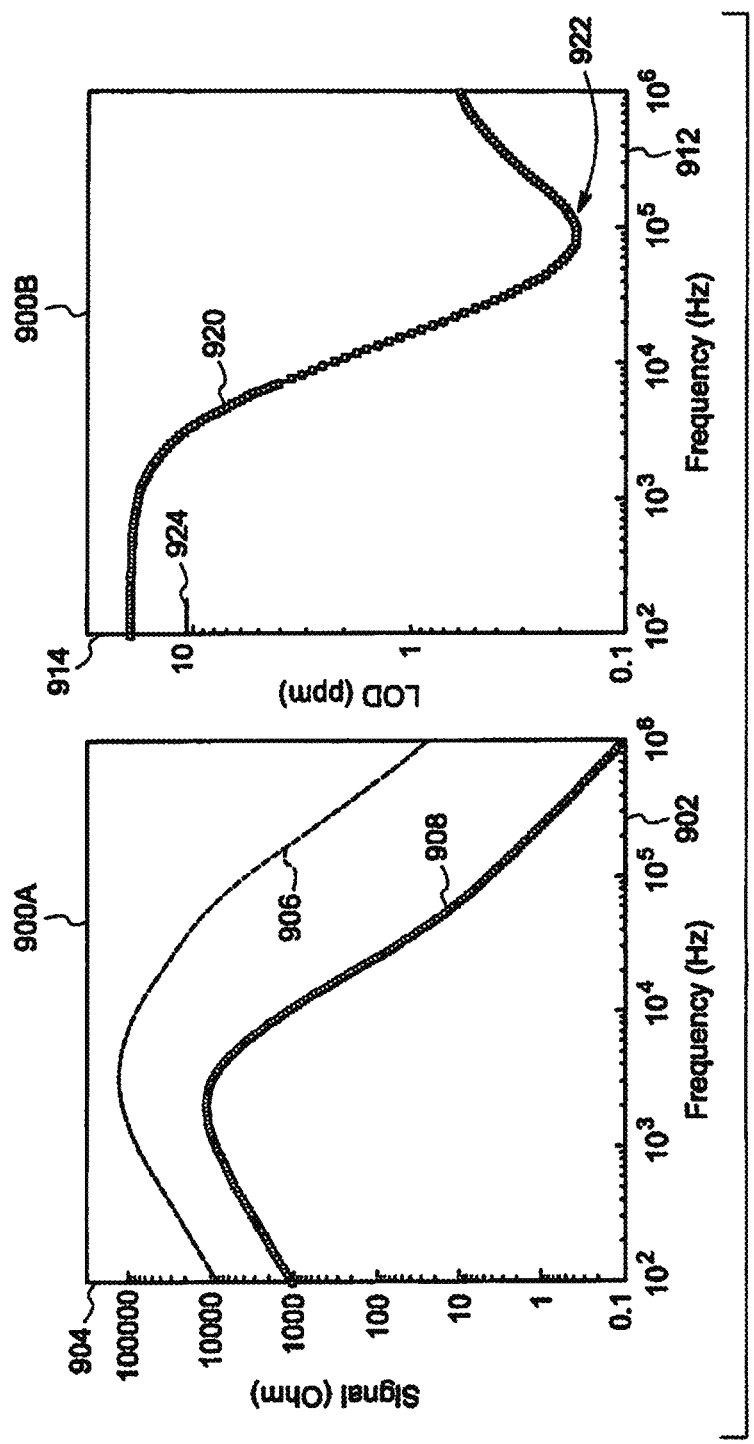
FIG. 10 depicts graphical illustrations of effects of operation frequencies on the quality of a hydrogen sensor response defined as a limit of detection, in accordance with one embodiment.

In one embodiment, the limit of detection at different frequencies of sensor operation from about 100 Hz to about 1 MHZ can be calculated for an imaginary part of the impedance response. Baseline noise a was taken at three locations of the sensor operation as illustrated by the baselines 810, 812, 814 illustrated in graphs 800A and 800C of FIG. 9. FIG. 10 illustrates graphical illustrations of effects of operation frequencies on the quality of the hydrogen sensor response defined as the limit of detection, in accordance with one embodiment. Graph 900A includes a horizontal axis 902 representative of frequency, and a vertical axis representative of increasing values of resistance. The graph 900A illustrates the value of the baseline noise a illustrated as signal line 908 over the measured frequency response of the sensor. The sensor response S at the smallest measured gas concentration of about 50 ppm is shown as signal line 906. As illustrated in graph 900A, the signal line 908 indicating the baseline noise σ and the signal line 906 indicating the sensor response S do not track each other at the measured frequencies. For example, the sensor linearity is not the same at different frequencies.

Alternatively, graph 900B illustrates the limit of detection as calculated based on Equation 1. The graph 900B includes a horizontal axis 912 representative of frequency, and a vertical axis 914 representative of increasing parts per million values of a limit of detection. A signal line 920 indicates the calculated limit of detection for the imaginary part of the impedance response of the sensor 114. A minimum limit of detection at a point 922 represents about 0.18 ppm of hydrogen at about 0.1 MHz. Alternatively, a point 924 represents a calculated limit of detection from the resistance measurements (illustrated in graph 800A shown in FIG. 9) of about 10.5 ppm of hydrogen. For example, the limit of detection of the impedance response of the sensor was improved by about 58 times relative to the limit of detection of the resistance response of the sensor.

Figure 11:
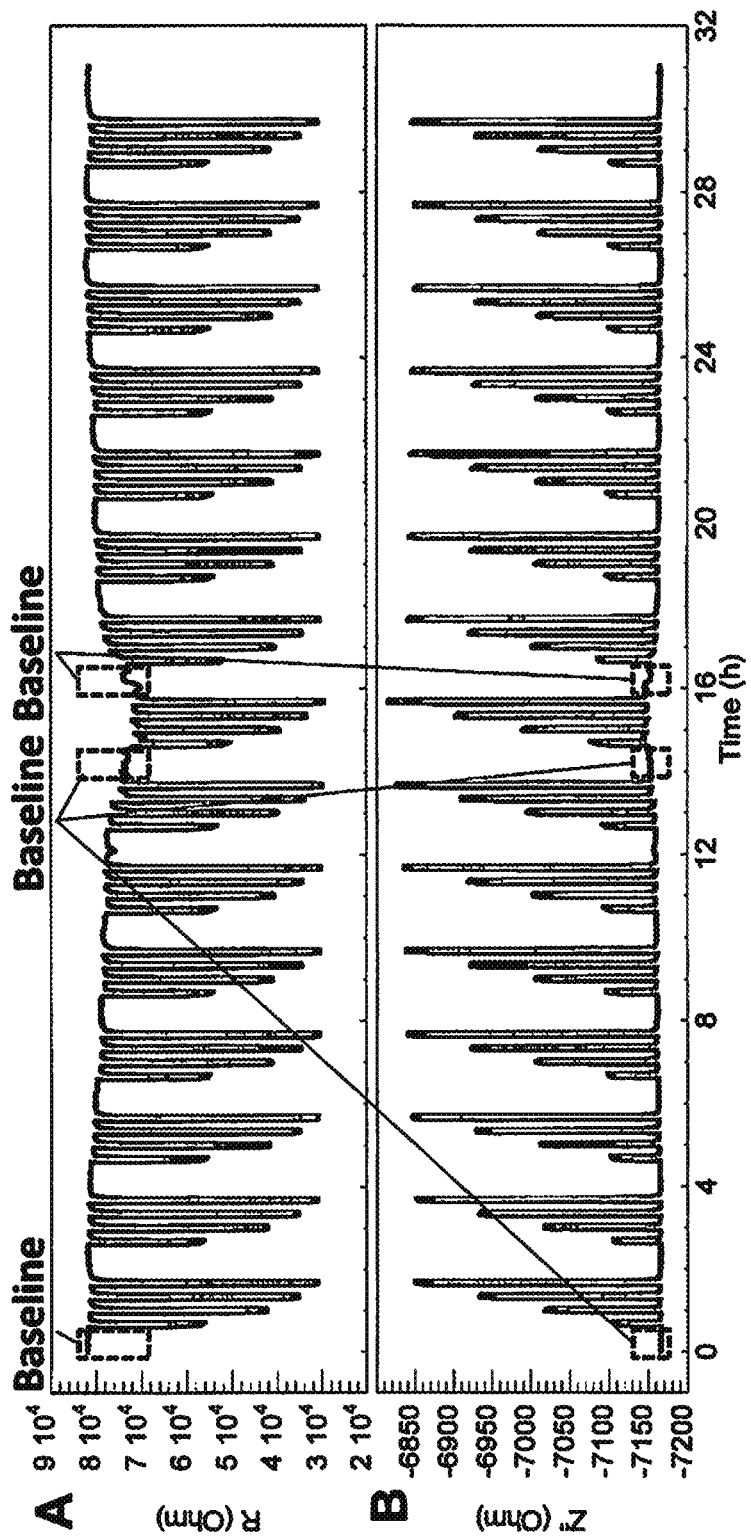
FIG. 11 depicts graphical illustrations of resistance changes and impedance changes of a methane sensor response to exposure of hydrogen gas in accordance with one embodiment.

FIG. 11 illustrates graphical illustrations A, B of resistance changes and impedance changes of a methane sensor response to exposure of methane gas in accordance with one embodiment. The response of the sensor to methane concentrations was tested over the test time of 30 h. Exposures were performed to methane gas concentrations such as 1, 2, 3, and 4 ppm. Illustration A in FIG. 11 shows the resistance change of the sensor where the sensor depicts a significant fluctuation of a baseline in addition to the response to methane. It has been discovered that operation of the sensor in the impedance mode has a significantly less contributions of fluctuations to or in the baseline as compared to resistance measurements (see the illustration B in FIG. 11).

A limit of detection at different frequencies of the sensor operation was calculated from 20 Hz to 1 MHz for the Z" of the sensor response. The baseline noise was taken at three locations of the sensor operation as illustrated in the dotted boxes in illustrations A and B in FIG. 11.

Figure 12:
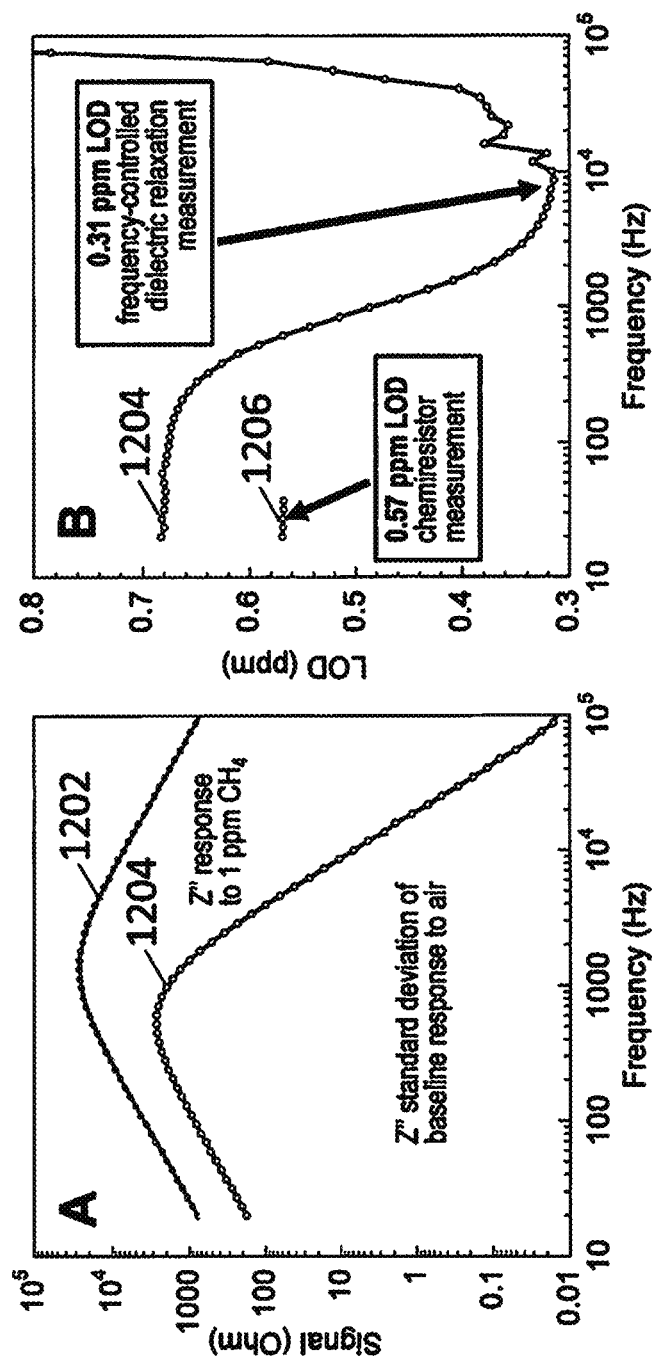
FIG. 12 depicts graphical illustrations of effects of operation frequencies on the quality of a methane sensor response defined as a limit of detection, in accordance with one embodiment.

FIG. 12 illustrates graphical illustrations A, B of effects of operation frequencies on the quality of a methane sensor response defined as the limit of detection, in accordance with one embodiment. This value of baseline response (noise) is illustrated in illustration A in FIG. 12 as data points over the measured frequency response of the sensor. The sensor response S at its smallest measured gas concentration of 1 ppm is depicted in data points 1202, indicating that data points 1204 and data points 1202 do not track each other well at the measurement frequencies, which is expected because the sensor linearity is not the same at different frequencies. Thus, when the limit of detection for Z" response is calculated, this result is depicted in illustration B of FIG. 12. This illustration shows the existence of the minimum in the limit of detection of 0.31 ppm of methane at 0.01 MHz. For comparison, from the resistance measurements (illustration A in FIG. 11), the calculated limit of detection was 0.57 ppm of methane also shown in illustration B of FIG. 12 as data points 1206.

Figure 13:
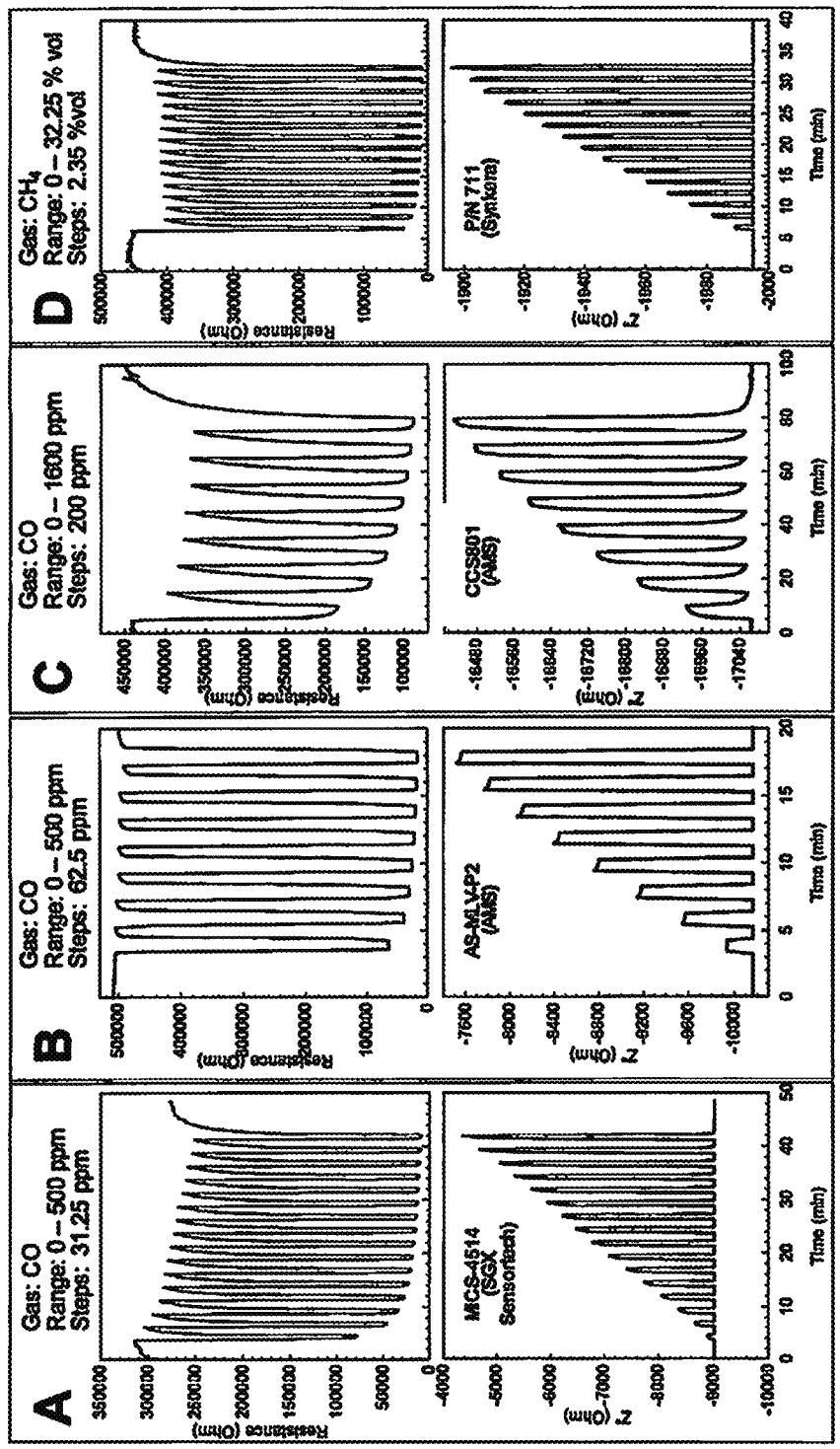
FIG. 13 depicts graphical illustrations of responses of different types of metal oxide semiconductor sensing elements to carbon monoxide and methane gases measured using conventional resistance and dielectric excitation measurements, in accordance with one embodiment.
Figure 14:
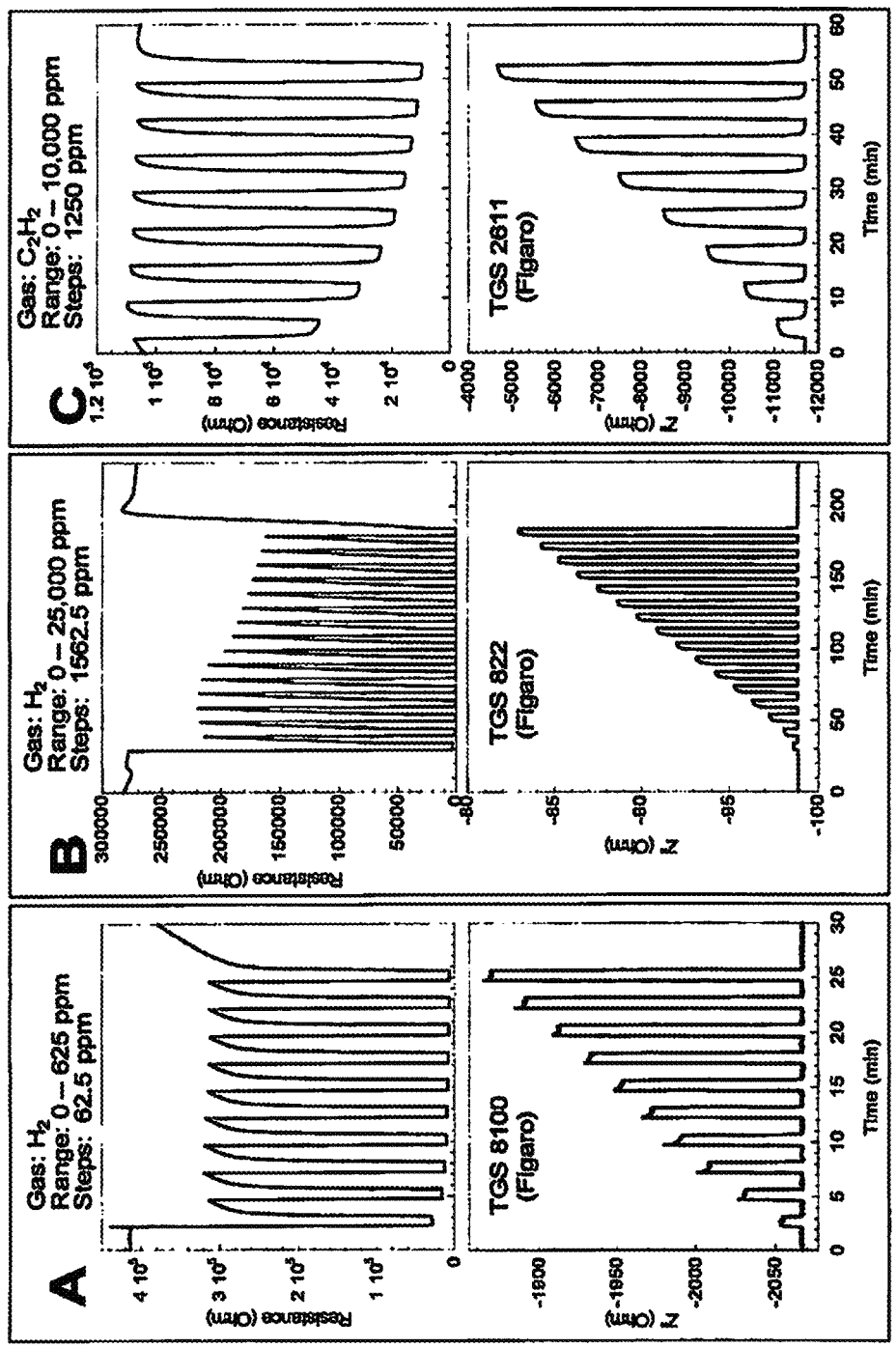
FIG. 14 depicts graphical illustrations of responses of different types of metal oxide semiconductor sensing elements to hydrogen and acetylene gases measured using conventional resistance and dielectric excitation measurements, in accordance with one embodiment.
Figure 15:
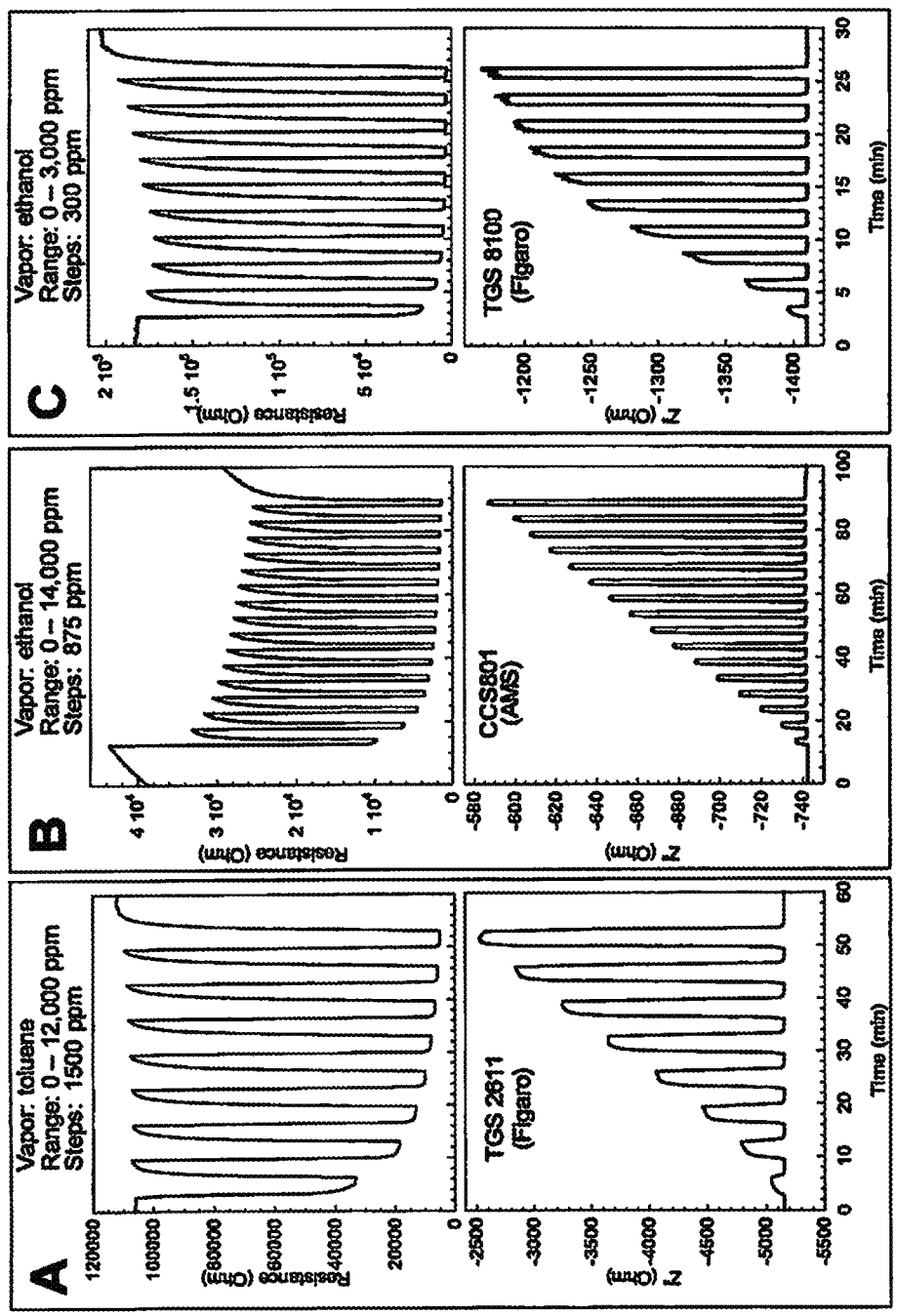
FIG. 15 depicts graphical illustrations of responses of different types of metal oxide semiconductor sensing elements to toluene and ethanol vapors measured using conventional resistance and dielectric excitation measurements, in accordance with one embodiment.

FIGS. 13, 14, and 15 present illustrations of examples of responses of different types of MOS sensing elements to different gases and vapors such as carbon monoxide (CO), methane ($CH_4$), hydrogen ($H_2$), acetylene ($C_2H_2$), toluene, and ethanol. These examples illustrate that diverse types of MOS sensing elements follow the rule of more linear response of the dielectric excitation measurements at the shoulder of the dielectric relaxation peak of the Zim impedance spectrum as compared to resistance measurements.

FIG. 13 depicts responses of four types of MOS sensing elements to (A-C) CO and (D) $CH_4$ measured using conventional resistance (top graphs) and dielectric excitation measurements (bottom graphs). Illustration A in FIG. 13 depicts responses of sensor MiCS-4514 (SGX Sensortech, Switzerland) to CO gas in the range 0-500 ppm with steps of 31.25 ppm. Illustration B in FIG. 13 depicts responses of sensor AS-MLV-P2 (ams AG, Austria) to CO gas in the range 0-500 ppm with steps of 62.5 ppm. Illustration C in FIG. 13 depicts responses of sensor CCS801 (ams AG, Austria) to CO gas in the range 0-1600 ppm with steps of 200 ppm. Illustration D in FIG. 13 depicts responses of sensor P/N 711 (Synkera Technologies, Inc. Longmont, Colo., USA) to $CH_4$ gas in the range 0-32.25% vol with steps of 2.35% vol.

The illustrations in FIG. 14 depict responses of three types of MOS sensing elements to (A-B) $H_2$ and (C) $C_2H_2$ measured using conventional resistance (top graphs) and dielectric excitation measurements (bottom graphs). Illustration A in FIG. 14 depicts responses of sensor TGS 8100 (Figaro USA, Inc., Arlington Heights, Ill., USA) to $H_2$ gas in the range 0-625 ppm with steps of 62.5 ppm. Illustration B in FIG. 14 depicts responses of sensor TGS 822 (Figaro USA, Inc., Arlington Heights, Ill., USA) to $H_2$ gas in the range 0-25,000 ppm with steps of 1562.5 ppm. Illustration C in FIG. 14 depicts responses of sensor TGS 2611 (Figaro USA, Inc., Arlington Heights, Ill., USA) to $C_2H_2$ gas in the range 0-10,000 ppm with steps of 1250 ppm.

The illustrations of FIG. 15 depict responses of three types of MOS sensing elements to (A) toluene and (B,C) ethanol vapors measured using conventional resistance (top graphs) and dielectric excitation measurements (bottom graphs). Illustration A of FIG. 15 depicts responses of sensor TGS 2611 (Figaro USA, Inc., Arlington Heights, Ill., USA) to toluene vapor in the range 0-12,000 ppm with steps of 1500 ppm. Illustration B of FIG. 15 depicts responses of sensor CCS801 (ams AG, Austria) to ethanol vapor in the range 0-14,000 ppm with steps of 875 ppm. Illustration C of FIG. 15 depicts responses of sensor TGS8100 (Figaro USA, Inc., Arlington Heights, Ill., USA) to ethanol vapor in the range 0-3,000 ppm with steps of 300 ppm.

In one embodiment, a gas sensor system includes a gas sensing element that includes a gas sensing material and electrodes configured to apply electrical stimuli to the gas sensing material and one or more processors configured to control the gas sensing element. The one or more processors are configured to direct the electrodes to apply the electrical stimuli at two or more different electrical excitation frequencies to the gas sensing material. A first electrical excitation frequency of the two or more different electrical excitation frequencies is configured to provide a quantitative gas response of the gas sensing material, the quantitative gas response including a response drift. A second electrical excitation frequency of the two or more different electrical excitation frequencies is configured to provide a baseline response of the gas sensing material based at least in part on the response drift.

Optionally, one or more processors are configured to direct the electrodes to apply the second electrical excitation frequency when the gas sensor system is in an operating state.

Optionally, the one or more processors are configured to operate in a gas response mode or in a baseline correction mode.

Optionally, the one or more processors are configured to receive the baseline response from the gas sensing element responsive to the one or more processors operating in the gas response mode.

Optionally, the one or more processors are configured to correct the baseline response responsive to the one or more processors operating in the baseline correction mode.

Optionally, the second electrical excitation frequency is configured to utilize the response drift of the quantitative gas response of the gas sensing material to move the quantitative gas response toward a target threshold of the quantitative gas response.

Optionally, the one or more processors are configured to determine an amount of the response drift of the quantitative gas response of the gas sensing material.

Optionally, the response drift of the quantitative gas response varies over time. The one or more processors can be configured to determine a gas of interest responsive to the varying response drift.

Optionally, the one or more processors are configured to determine a difference between the quantitative gas response and the baseline response.

Optionally, the second electrical excitation frequency is configured to improve a limit of detection of the quantitative gas response of the gas sensing material relative to the first electrical excitation frequency.

Optionally, the quantitative gas response includes an impedance response of the gas sensing material.

Optionally, the first electrical excitation frequency is configured to provide a quantitative linear response of the gas sensing material to gas concentrations.

In one embodiment, a method includes applying a first electrical stimuli to a gas sensing material of a gas sensing element via electrodes at a first electrical excitation frequency and receiving a quantitative gas response of the gas sensing material responsive to applying the first electrical stimuli at the first electrical excitation frequency to the gas sensing material. The quantitative gas response includes a response drift. The method also includes applying a second electrical stimuli to the gas sensing material of the gas sensing element via the electrodes at a second electrical excitation frequency. The second electrical excitation frequency is configured to provide a baseline response of the gas sensing material to the response drift.

Optionally, applying the first electrical stimuli at the first electrical excitation frequency and applying the second electrical stimuli at the second electrical excitation frequency when the gas sensor system is in an operating state.

Optionally, the method also includes operating the gas sensing element in a gas response mode or in a baseline correction mode.

Optionally, the method also includes receiving the baseline response from the gas sensing element responsive to operating in the gas response mode.

Optionally, the method also includes correcting the baseline response from the gas sensing element responsive to operating in the baseline correction mode.

Optionally, the method also includes utilizing the response drift of the quantitative gas response of the gas sensing material to move the quantitative gas response toward a target threshold of the quantitative gas response.

Optionally, the method also includes determining an amount of the response drift of the quantitative gas response of the gas sensing material.

Optionally, the method also includes determining a gas of interest responsive to the response drift of the quantitative gas response of the gas sensing material varying over time.

Optionally, the method also includes determining a difference between the quantitative gas response and the baseline response.

Optionally, the second electrical excitation frequency is configured to improve a limit of detection of the quantitative gas response of the gas sensing material relative to the first electrical excitation frequency.

Optionally, the quantitative gas response includes an impedance response of the gas sensing material.

Optionally, a first electrical excitation frequency is configured to provide a quantitative linear response of the gas sensing material to gas concentrations.

In one embodiment, a gas sensor system includes a gas sensing element that includes a gas sensing material and electrodes configured to apply electrical stimuli to the gas sensing material and one or more processors configured to control the gas sensing element. The one or more processors are configured to direct the electrodes to apply the electrical stimuli at two or more different electrical excitation frequencies to the gas sensing material when the gas sensor system is in an operating state. A first electrical excitation frequency of the two or more different electrical excitation frequencies is configured to provide a quantitative gas response of the gas sensing material. A second electrical excitation frequency of the two or more different electrical excitation frequencies is configured to improve a limit of detection of a gas of interest of the quantitative gas response of the gas sensing material relative to the first electrical excitation frequency.

In one embodiment, a gas sensor system includes a gas sensing element that includes a gas sensing material and electrodes configured to apply electrical stimuli to the gas sensing material and one or more processors configured to control the gas sensing element, wherein the one or more processors are configured to direct the electrodes to apply the electrical stimuli at two or more different electrical excitation conditions to the gas sensing material. A first electrical excitation condition of the two or more different electrical excitation conditions is configured to provide a quantitative gas response of the gas sensing material, the quantitative gas response including a response drift. A second electrical excitation condition of the two or more different electrical excitation conditions is configured to provide a baseline response of the gas sensing material based at least in part on the response drift.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "including," or "having" (or like terms) an element, which has a particular property or a plurality of elements with a particular property, may include additional such elements that do not have the particular property.

As used herein, terms such as "system" or "controller" may include hardware and/or software that operate(s) to perform one or more functions. For example, a system or controller may include a computer processor or other logic-based device that performs operations based on instructions stored on a tangible and non-transitory computer readable storage medium, such as a computer memory. Alternatively, a system or controller may include a hard-wired device that performs operations based on hard-wired logic of the device. The systems and controllers shown in the figures may represent the hardware that operates based on software or hardwired instructions, the software that directs hardware to perform the operations, or a combination thereof.

As used herein, terms such as "operably connected," "operatively connected," "operably coupled," "operatively coupled," "operationally contacted," "operational contact" and the like indicate that two or more components are connected in a manner that enables or allows at least one of the components to carry out a designated function. For example, when two or more components are operably connected, one or more connections (electrical and/or wireless connections) may exist that allow the components to communicate with each other, that allow one component to control another component, that allow each component to control the other component, and/or that enable at least one of the components to operate in a designated manner.

It is to be understood that the subject matter described herein is not limited in its application to the details of construction and the arrangement of elements set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A gas sensor system, comprising:
   a gas sensing element that includes a gas sensing material and electrodes configured to apply electrical stimuli at two or more electrical excitation frequencies to the gas sensing material; and
   one or more processors configured to control the gas sensing element, wherein the one or more processors are configured to instruct the electrodes to apply a first electrical stimulus to the gas sensing material at a first time period and to apply a second electrical stimulus to the gas sensing material at a second time period while the gas sensing material is exposed to a gas, wherein a first electrical excitation frequency of the first electrical stimulus is different than a second electrical excitation frequency of the second electrical stimulus, wherein the first electrical excitation frequency is configured to provide a quantitative gas response of the gas sensing material, wherein the quantitative gas response generated via application of the first electrical excitation frequency is effectuated by a presence of the gas and includes a response drift, and wherein the second electrical excitation frequency is configured to provide a baseline response of the gas sensing material, wherein the baseline response generated via application of the second electrical excitation frequency is independent of the presence of the gas.

2. The gas sensor system of claim 1, wherein the one or more processors are configured to instruct the electrodes to apply the second electrical excitation frequency when the gas sensor system is in an operating state.

3. The gas sensor system of claim 1, wherein the one or more processors are configured to operate in a gas response mode or in a baseline correction mode.

4. The gas sensor system of claim 3, wherein the one or more processors are configured to receive the baseline response from the gas sensing element responsive to the one or more processors operating in the gas response mode.

5. The gas sensor system of claim 4, wherein the one or more processors are configured to correct the baseline response responsive to the one or more processors operating in the baseline correction mode.

6. The gas sensor system of claim 1, wherein the second electrical excitation frequency is configured to utilize the response drift of the quantitative gas response of the gas sensing material to move the quantitative gas response toward a target threshold of the quantitative gas response.

7. The gas sensor system of claim 1, wherein the one or more processors are configured to determine an amount of the response drift of the quantitative gas response of the gas sensing material.

8. The gas sensor system of claim 1, wherein the response drift of the quantitative gas response varies over time, wherein the one or more processors are configured to determine a gas of interest responsive to the varying response drift.

9. The gas sensor system of claim 1, wherein the one or more processors are configured to determine a difference between the quantitative gas response and the baseline response.

10. The gas sensor system of claim 1, wherein the second electrical excitation frequency is configured to improve a limit of detection of the quantitative gas response of the gas sensing material relative to the first electrical excitation frequency.

11. The gas sensor system of claim 1, wherein the quantitative gas response includes an impedance response of the gas sensing material.

12. The gas sensor system of claim 1, wherein the first electrical excitation frequency is configured to provide a quantitative linear response of the gas sensing material to gas concentrations.

13. A method, comprising:
    applying, while a gas sensing material of a gas sensing element is exposed to a gas, first electrical stimuli to the gas sensing material via electrodes at a first electrical excitation frequency, wherein the first electrical excitation frequency is configured to provide a quantitative gas response of the gas sensing material, wherein the quantitative gas response generated via application of the first electrical stimuli is effectuated by a presence of the gas and includes a response drift;
    receiving the quantitative gas response of the gas sensing material responsive to applying the first electrical stimuli at the first electrical excitation frequency to the gas sensing material; and
    applying, while the gas sensing material is exposed to the gas, second electrical stimuli to the gas sensing material via the electrodes at a second electrical excitation frequency, wherein the first electrical excitation frequency is different than the second electrical excitation frequency, wherein the second electrical excitation frequency is configured to provide a baseline response of the gas sensing material, and wherein the baseline response generated via application of the second electrical stimuli is independent of the presence of the gas.

14. The method of claim 13, further comprising applying the first electrical stimuli at the first electrical excitation frequency and applying the second electrical stimuli at the second electrical excitation frequency when the gas sensing element is in an operating state.

15. The method of claim 13, further comprising operating the gas sensing element in a gas response mode or in a baseline correction mode.

16. The method of claim 15, further comprising receiving the baseline response from the gas sensing element responsive to operating in the gas response mode.

17. The method of claim 16, further comprising correcting the baseline response from the gas sensing element responsive to operating in the baseline correction mode.

18. The method of claim 13, further comprising utilizing the response drift of the quantitative gas response of the gas sensing material to move the quantitative gas response toward a target threshold of the quantitative gas response.

19. The method of claim 13, further comprising determining an amount of the response drift of the quantitative gas response of the gas sensing material.

20. The method of claim 13, further comprising determining a gas of interest responsive to the response drift of the quantitative gas response of the gas sensing material varying over time.

21. The method of claim 13, further comprising determining a difference between the quantitative gas response and the baseline response.

22. The method of claim 13, wherein the second electrical excitation frequency is configured to improve a limit of detection of the quantitative gas response of the gas sensing material relative to the first electrical excitation frequency.

23. The method of claim 13, wherein the quantitative gas response includes an impedance response of the gas sensing material.

24. The method of claim 13, wherein the first electrical excitation frequency is configured to provide a quantitative linear response of the gas sensing material to gas concentrations.

25. A gas sensor system, comprising:
   a gas sensing element that includes a gas sensing material and electrodes configured to apply electrical stimuli to the gas sensing material at two or more electrical excitation frequencies; and
   one or more processors configured to control the gas sensing element, wherein the one or more processors are configured to instruct the electrodes to apply a first electrical stimulus to the gas sensing material and to apply a second electrical stimulus to the gas sensing material when the gas sensor system is in an operating state and while the gas sensing material is exposed to a gas of interest,
   wherein a first electrical excitation frequency of the first electrical stimulus is different than a second electrical excitation frequency of the second electrical stimulus,
   wherein the first electrical excitation frequency is configured to provide a quantitative gas response of the gas sensing material, wherein the quantitative gas response generated via application of the first electrical excitation frequency is effectuated by a presence of the gas of interest and includes a response drift, and
   wherein the second electrical excitation frequency is configured to provide a baseline response of the gas sensing material to improve a limit of detection of the gas of interest, wherein the baseline response generated via application of the second electrical excitation frequency is independent of the presence of the gas of interest.

26. A gas sensor system, comprising:
   a gas sensing element that includes a gas sensing material and electrodes configured to apply electrical stimuli to the gas sensing material; and
   one or more processors configured to control the gas sensing element, wherein the one or more processors are configured to instruct the electrodes to apply a first electrical stimulus to the gas sensing material and to apply a second electrical stimulus to the gas sensing material while the gas sensing material is exposed to a gas, wherein a first electrical excitation frequency of the first electrical stimulus is different than a second electrical excitation frequency of the second electrical stimulus,
   wherein the first electrical excitation frequency is configured to provide a quantitative gas response of the gas sensing material, wherein the quantitative gas response generated via application of the first electrical excitation frequency is effectuated by a presence of the gas and includes a response drift, and
   wherein the second electrical excitation frequency is configured to provide a baseline response of the gas sensing material, wherein the baseline response generated via application of the second electrical excitation frequency is independent of the presence of the gas.

* * * * *